(12) United States Patent
Bader et al.

(10) Patent No.: US 9,139,640 B2
(45) Date of Patent: Sep. 22, 2015

(54) SHORTENED TETRANECTIN-APOLIPOPROTEIN A-1 FUSION PROTEIN, A LIPID PARTICLE CONTAINING IT, AND USES THEREOF

(71) Applicant: Hoffmann-La Roche Inc., Little Falls, NJ (US)

(72) Inventors: Martin Bader, Penzberg (DE); Roberto Falkenstein, Munich (DE); Christian Schantz, Penzberg (DE)

(73) Assignee: Hoffmann-La Roche Inc., Little Falls, NJ (US)

(*) Notice: Subject to any disclaimer, the term of this patent is extended or adjusted under 35 U.S.C. 154(b) by 0 days.

(21) Appl. No.: 14/315,187

(22) Filed: Jun. 25, 2014

(65) Prior Publication Data

US 2015/0011459 A1    Jan. 8, 2015

Related U.S. Application Data

(63) Continuation of application No. 13/592,183, filed on Aug. 22, 2012, now Pat. No. 8,791,063.

(30) Foreign Application Priority Data

Aug. 25, 2011  (EP) .................................... 11178746

(51) Int. Cl.
*C07K 14/775* (2006.01)
*C07K 14/705* (2006.01)
*C12N 15/62* (2006.01)

(52) U.S. Cl.
CPC ........... *C07K 14/775* (2013.01); *C07K 14/7056* (2013.01); *C12N 15/62* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 4,608,347 | A | 8/1986 | Bernstam |
| 5,928,644 | A | 7/1999 | Russell-Jones et al. |
| 6,291,245 | B1 | 9/2001 | Kopetzki et al. |
| 6,897,039 | B2 | 5/2005 | Graversen et al. |
| 2002/0142953 | A1 | 10/2002 | Ballinger et al. |
| 2002/0156007 | A1 | 10/2002 | Graversen et al. |
| 2005/0176625 | A1 | 8/2005 | Curstedt et al. |
| 2005/0287636 | A1 | 12/2005 | Cho |
| 2006/0217312 | A1 | 9/2006 | Dasseux |
| 2009/0246859 | A1 | 10/2009 | Domanico et al. |
| 2010/0028995 | A1 | 2/2010 | Graversen et al. |
| 2010/0189774 | A1 | 7/2010 | Lenormand |
| 2012/0190609 | A1 | 7/2012 | Bader et al. |
| 2012/0190610 | A1 | 7/2012 | Bader et al. |
| 2012/0214200 | A1 | 8/2012 | Grossmann et al. |
| 2013/0053551 | A1 | 2/2013 | Falkenstein et al. |

FOREIGN PATENT DOCUMENTS

| | | |
|---|---|---|
| EP | 0972838 B1 | 9/2004 |
| EP | 1 486 571 B1 | 12/2005 |
| EP | 1 422 237 B1 | 2/2007 |
| WO | 93/12143 A1 | 6/1993 |
| WO | 98/56906 A1 | 12/1998 |
| WO | 99/16409 A2 | 4/1999 |
| WO | 02/38609 A2 | 5/2002 |
| WO | 03/096983 A2 | 11/2003 |
| WO | 03/097695 A1 | 11/2003 |
| WO | 03/097696 A1 | 11/2003 |
| WO | 2005/041886 A2 | 5/2005 |
| WO | 2005/065708 A2 | 7/2005 |
| WO | 2005/084642 A1 | 9/2005 |
| WO | 2006/039622 A2 | 4/2006 |
| WO | 2006/047614 A2 | 5/2006 |
| WO | 2006/069371 A1 | 6/2006 |
| WO | 2006/100567 A1 | 9/2006 |
| WO | 2006/125304 A1 | 11/2006 |
| WO | 2007/098122 A2 | 8/2007 |
| WO | 2007/137400 A1 | 12/2007 |
| WO | 2008013885 A2 | 1/2008 |
| WO | 2008/017906 A1 | 2/2008 |
| WO | 2008/094905 A2 | 8/2008 |
| WO | 2008/106660 A2 | 9/2008 |
| WO | 2008/156873 A2 | 12/2008 |
| WO | 2009/036460 A2 | 3/2009 |
| WO | 2009/097587 A2 | 8/2009 |
| WO | 2009/131704 A2 | 10/2009 |
| WO | 2010/083611 A1 | 7/2010 |
| WO | 2012/028522 A1 | 3/2012 |
| WO | 2012/028526 A2 | 3/2012 |
| WO | 2012/028526 A3 | 3/2012 |
| WO | 2013/127700 A1 | 9/2013 |
| WO | 2013/127816 A1 | 9/2013 |
| WO | 2013127752 A1 | 9/2013 |

OTHER PUBLICATIONS

Beck and Zink, "Nucleotide sequence and genome organisation of filamentous bacteriophages fl and fd" Gene 16(1-3):35-58 (1981).
Bujard et al., "A T5 promoter-based transcription-translation system for the analysis of proteins in vitro and in vivo" Methods Enzymol. 155:416-33 (1987).
Chen et al., "Apolipoprotein AI tertiary structures determine stability and phospholipid-binding activity of discoidal high-density lipoprotein particles of different sizes" Protein Sci. 18(5):921-35 (2009).
Farabaugh et al., "Sequence of the lacI gene" Nature 274:765-9 (1978).
Graversen et al., "Trimerization of apolipoprotein A-I retards plasma clearance and preserves antiatherosclerotic properties" J Cardiovasc Pharmacol. 51(2):170-7. (2008).
Jonas et al., "Reconstitution of high-density lipoproteins" Methods Enzymol. 128:553-82 (1986).

(Continued)

*Primary Examiner* — Amber D Steele
*Assistant Examiner* — Schuyler Milton
(74) *Attorney, Agent, or Firm* — Jennifer K. Holmes

(57) ABSTRACT

Herein is reported a shortened tetranectin-apolipoprotein A-I fusion protein and a lipid particle comprising the shortened tetranectin-apolipoprotein A-I fusion protein as well as uses thereof.

16 Claims, 13 Drawing Sheets

(56) References Cited

OTHER PUBLICATIONS

Jonas, "A review of plasma apolipoprotein A-I interactions with phosphatidylcholines" Exp Lung Res. 6(3-4):255-70 ( 1984).

Kuksis, Lecithins "Chapter Seven—Animal Lecithins" B.F. Szhuaj and G.R. List, American Oil Chemists' Society,:105-162 ( 1985).

Levy et al., "Reconstitution of the sarcoplasmic reticulum Ca(2+)-ATPase: mechanisms of membrane protein insertion into liposomes during reconstitution procedures involving the use of detergents" Biochem Biophys Acta. 1107(2):293-98 ( 1992).

Marchesi et al., "Apolipoprotein A-IMilano/POPC complex attenuates post-ischemic ventricular dysfunction in the isolated rabbit heart" Atherosclerosis 197(2):572-8 ( 2008).

Matz et al., "Micellar complexes of human apolipoprotein A-I with phosphatidylcholines and cholesterol prepared from cholate-lipid dispersions" J Biol Chem. 257(8):4535-40 ( 1982).

Nissen et al., "Effect of recombinant ApoA-I Milano on coronary atherosclerosis in patients with acute coronary syndromes: a randomized controlled trial" JAMA 290(17):2292-300 ( 2003).

PCT ISR for PCT/EP2012/066301.

PCT Written Opinion of the ISA for PCT/EP2012/066301.

Queen et al., "A humanized antibody that binds to the interleukin 2 receptor" Proc. Natl. Acad. Sci USA 86:10029-10033 ( 1989).

Reichmann et al., "Reshaping human antibodies for therapy" Nature 332:323-327 (Mar. 24, 1988).

Riesenberg et al., "High cell density cultivation of *Escherichia coli* at controlled specific growth rate" J Biotechnol. 20(1):17-27 (Aug. 1991).

Rose et al., "Structure and function of the yeast URA3 gene: expression *Escherichia coli*" Gene 29(1-2):113-24 ( 1984).

Santos et al., "Na,K-ATPase reconstituted in liposomes: effects of lipid composition" and Surfaces B: Biointerfaces 41(4):239-248 ( 2005).

Schwarz et al., "Nucleotide sequence of cro, cII and part of the O gene in phage λ DNA 410" Nature 272:410-14 ( 1978).

Seddon et al., "Membrane proteins, lipids and detergents: not just a soap" Biochem Biophys Acta. 1666(1-2):105-17 ( 2004).

Shay et al., "High-productivity fermentation process for cultivating industrial microorganisms" Journal of Industrial Microbiology & Biotechnology 2:79-85 ( 1987).

Sirtori et al., "High Density Lipoprotein Administration: A New Therapeutic Modality for the Treatment of Cardiovascular Diseases" Curr Med Chem Immunol Endocr Metab Agents 5(4):321-33 ( 2005).

Stuber et al., "System for high level production in *E. coli* and rapid purification of recombinant proteins: application to epitope mapping, preparation of antibodies and structure-function analysis" Immunological methods, IV:121-152 ( 1990).

Sutcliffe et al., "Complete nucleotide sequence of the *Escherichia coli* plasmid pBR322" Cold Spring Hard Symp Quant Biol. 43(Pt 1):77-90 ( 1979).

UnitProt (APOA1_HUMAN, Polypeptide Sequence, Accession No. PO2647, pp. 1-6, (Jul. 21, 1986).

Dominiczak et al., "Apolipoproteins: Metabolic Role and Clinical Biochemistry Applications" Ann. Clinical Biochemistry 48:498-515 ( 2011).

Natarajan et al., "Identification of an Apolipoprotein A-I Structural Element that Mediates Cellular Cholesterol Efflux and Stabilizes ATP Binding Cassette Transporter A1" Journal of Biological Chemistry 279(23):24044-24052 ( 2004).

Scanu et al., "HDL: Bridging Past and Present With a Look at the Future" FASEB Journal 22:4044-4054 ( 2008).

Fig. 1
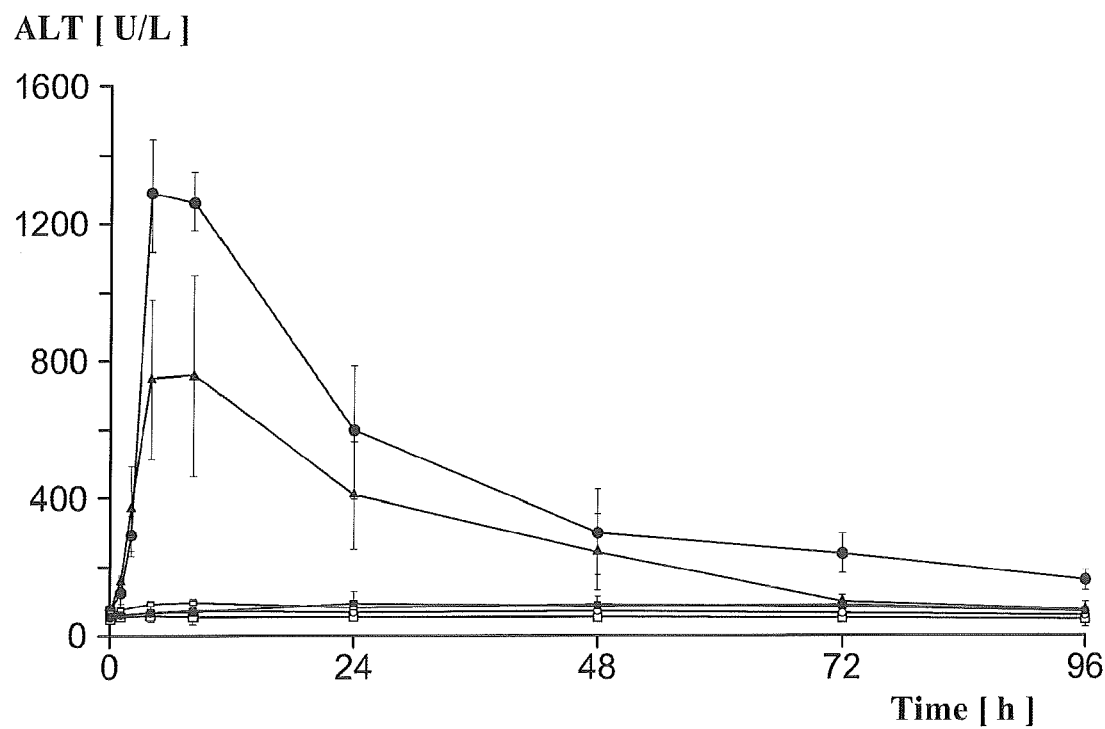
- ○ empty lipid particle
- □ POPC/DPPC (1:1)
- □ POPC
- ■ DPPC
- ▲ POPC/DPPC (3:1)
- ● DPPC/SM (9:1)
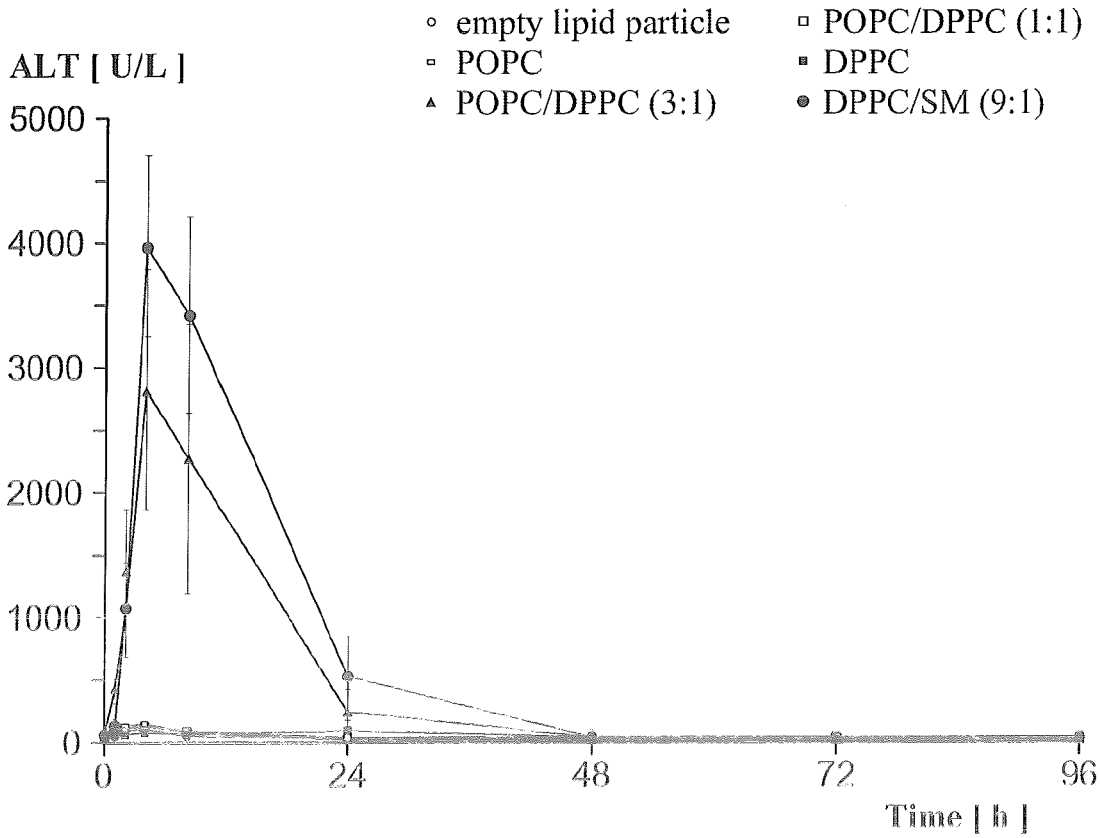

Fig. 12
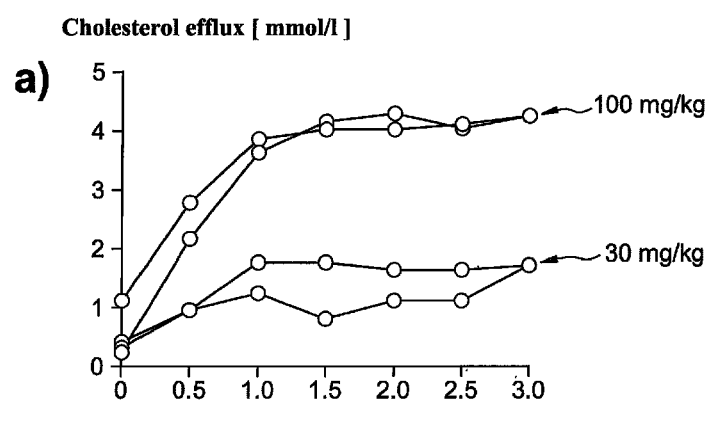
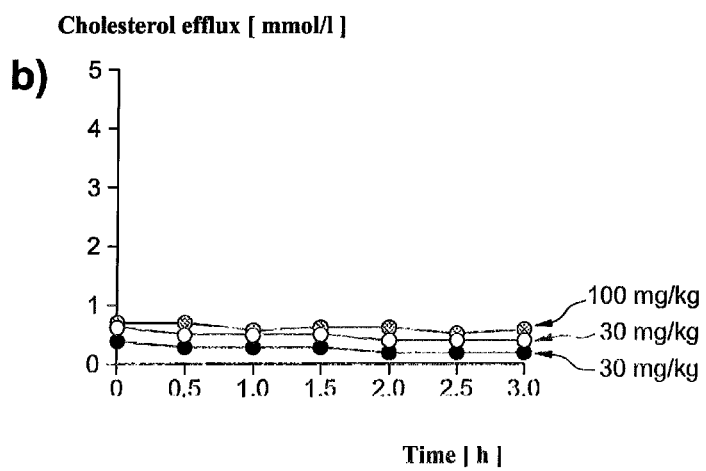

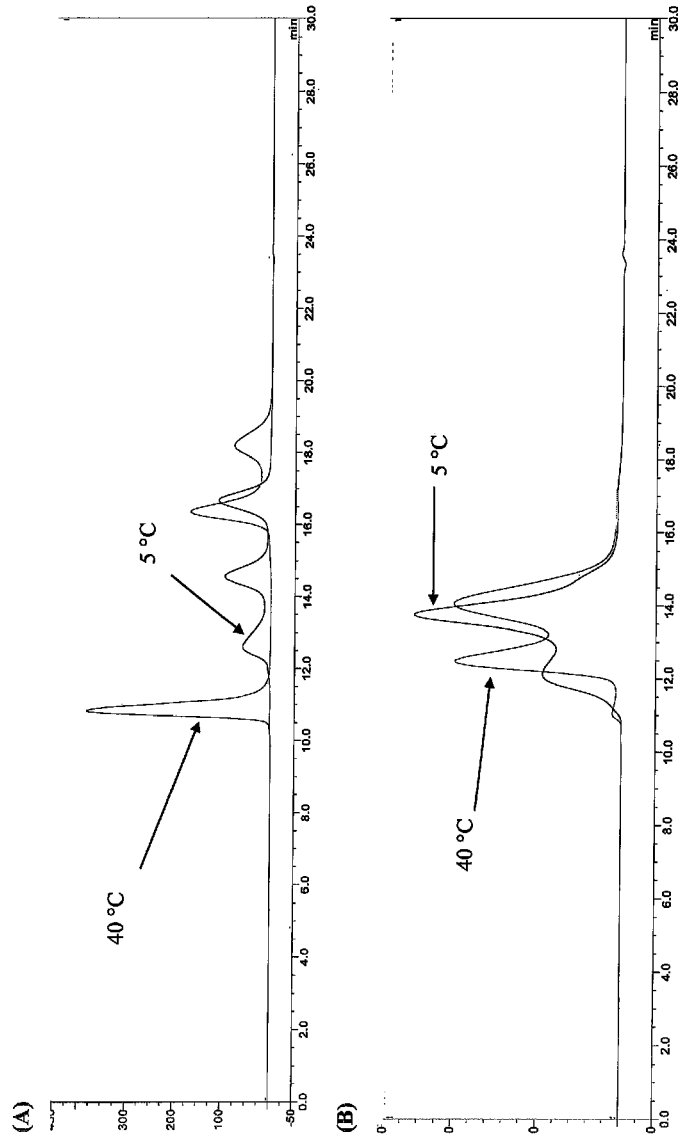

SHORTENED TETRANECTIN-APOLIPOPROTEIN A-1 FUSION PROTEIN, A LIPID PARTICLE CONTAINING IT, AND USES THEREOF

RELATED APPLICATIONS

This application is a continuation of U.S. Ser. No. 13/592,183, filed Aug. 22, 2012, which application claims the benefit of EP Application No. 11178746.1, filed Aug. 25, 2011. All the teachings of the above-referenced applications are incorporated herein by reference.

SEQUENCE LISTING

The instant application contains a Sequence Listing which has been submitted in ASCII format via EFS-Web and is hereby incorporated by reference in its entirety. Said ASCII copy, created on Jun. 25, 2014, is named P4756C1SeqList.txt and is 6,693 bytes in size.

FIELD OF THE INVENTION

The current invention is in the field of lipoproteins and lipid particles. Reported herein is a shortened tetranectin-apolipoprotein A-I fusion protein, a lipid particle, which comprises this shortened tetranectin-apolipoprotein A-I fusion protein and two different phosphatidylcholines, as well as uses of the fusion protein and the lipid particle.

BACKGROUND OF THE INVENTION

Plasma lipoproteins are soluble protein-lipid complexes that carry out lipid transport and metabolism in blood. Several major classes of lipoproteins are distinguished on the basis of their density, size, chemical compositions, and functions. Among them high-density-lipoprotein (HDL) particles alternatively denoted as high-density-lipid particles, are made up of several subclasses that vary in their average molecular weight of from 180 kDa to 360 kDa. Their average lipid and protein content is 50% by weight of each. Phosphatidylcholine (PC) accounts for 38% of the total lipid followed by cholesteryl esters and small amounts of other polar and non-polar lipids, including free cholesterol. The main protein component is apolipoprotein A-I (Apo A-I), representing about 60% of total protein weight in human HDL.

HDL particles and its major polypeptide apolipoprotein A-I participate in the reverse cholesterol transport (RCT). Therein the apolipoprotein A-I increases the efflux of cholesterol from cells, e.g. from cells of the wall of blood vessels, the binding of the lipid and the activation of the lecithin-cholesterol-acetyl-transferase and thereby the elimination of cholesterol via plasmatic flow by the liver. This is an active transport process involving the cell membrane protein ATP-binding-cassette-transporter-A-I (ABCA-I).

Apolipoprotein A-I and apolipoprotein-based therapeutics, e.g. reconstituted HDL particles, were already identified in the late 1970s and early 1980s of the last century. For apolipoprotein A-I-Milano containing lipid particles the clinical proof (meaning significant plaque reduction in arteriosclerotic patients) could be shown. Apolipoprotein A-I-Milano, a dimeric form of wild-type apolipoprotein A-I, was designed according to a naturally occurring mutant of the apolipoprotein A-I molecule. The dimer formation is enabled by the exchange of amino acid residue 173 (arginine) by cysteine allowing the formation of a disulfide bond.

In WO 2009/131704 nanostructures are reported, which are suitable for sequestering cholesterol and other molecules, comprising a core comprising an inorganic material. In WO 2006/125304 pharmaceutical compositions for treating or preventing coronary artery disease are reported. Compositions encoding apolipoproteins that are related to lipid metabolism and cardiovascular disease are reported in US 2002/0142953. In WO 2005/084642 an apoprotein-cochelate composition is reported. In WO 2009/036460 modified human apolipoprotein A-I polypeptides and their uses are reported. Plant production of dimeric and/or oligomeric forms of human apolipoprotein A-I protein muteins is reported in WO 2008/017906. In WO 2007/137400 a method and compound for the treatment of valvular stenosis is reported. In WO 2006/100567 charged lipoprotein complexes and their uses are reported.

In US 2002/0156007 apolipoprotein analogues are reported. Tetranectin trimerising polypeptides are reported in US 2010/0028995. In J. Cardiovas. Pharmacol. (51 (2008) 170-177) report Graversen, J. H., et al., that the trimerization of apolipoprotein A-I retards plasma clearance and preserves anti-atherosclerotic properties. High density lipoprotein administration—a new therapeutic modality for the treatment of cardiovascular disease is reported by Sirtori, C. R., et al. (Curr. Med. Chem. Immunol. Endocrine Metabol. Agents 5 (2005) 321-333).

In WO 03/097696 methods and compositions for the treatment of ischemic reperfusion are reported. Nanoscale bound bilayers, methods of use and production are reported in WO 2009/097587. In WO 2007/098122 methods for the treatment of macular degeneration and related eye conditions are reported. Apolipoprotein Analogues are reported in WO 02/38609. In WO 2005/041866 pharmaceutical formulations are reported. Methods and dosing regimens for the treatment and prevention of coronary syndromes are reported. Gene therapy, approaches to supply apolipoprotein A-I agonists and their use to treat dislipidemic disorders are reported in WO 99/16409. In WO 2008/106660 isolated phospholipid-protein particles are reported. Method for the prevention and treatment of diastolic dysfunction employing an apolipoprotein (APO A-I) mimetic peptide/phospholipid complex are reported in WO 2010/083611. In WO 2008/156873 APO A-I peptide mimetics are reported. Encapsulated HDL mimetic peptides are reported in WO 2008/094905. In WO 98/56906 a trimerising module is reported.

SUMMARY OF THE INVENTION

Herein is reported a shortened tetranectin-apolipoprotein A-I fusion protein with improved production properties, especially less expression side-product formation.

It has been found that the fraction of a shortened tetranectin-apolipoprotein A-I fusion protein starting with the amino acid residue proline (P) as the first encoded amino acid residue in crude *E. coli* cultivation supernatants is 90% or more, whereby the N-terminal methionine residue is removed efficiently.

One aspect as reported herein is a shortened tetranectin-apolipoprotein A-I fusion protein comprising the amino acid sequence of SEQ ID NO: 01 or a variant thereof, which has at least 70% sequence identity, as N-terminal amino acid sequence, whereby SEQ ID NO: 01 has the amino acid sequence (SEQ ID NO: 1)
PIVNAKKDVVNTKMFEELKSRLDTLAQEVALLKEQQALQTVDEPPQSPWD

RVKDLATVYVDVLKDSGRDYVSQFEGSALGKQLNLKLLDNWDSVTSTFSK

LREQLGPVTQEFWDNLEKETEGLRQEMSKDLEEVKAKVQPYLDDFQKKWQ

EEMELYRQKVEPLRAELQEGARQKLHELQEKLSPLGEEMRDRARAHVDAL

RTHLAPYSDELRQRLAARLEALKENGGARLAEYHAKATEHLSTLSEKAKP

ALEDLRQGLLPVLESFKVSFLSALEEYTKKLNTQ, and the variant has the N-terminal amino acid residues PIVN (residues 1-4 of SEQ ID NO:1).

One aspect as reported herein is a lipid particle comprising a shortened tetranectin-apolipoprotein A-I fusion protein as reported herein.

In one embodiment the lipid particle comprises a shortened tetranectin-apolipoprotein A-I fusion protein as reported herein and one or more lipids selected from phospholipid, lysophospholipid, galactocerebroside, ganglioside, cerebroside, glyceride, fatty acid, triglyceride, steroid lipid, cholesterol, cholesterol esters, or an analog or derivative thereof.

In one embodiment the lipid particle comprises
a) a shortened tetranectin-apolipoprotein A-I fusion protein as reported herein,
b) a phosphatidylcholine, and
c) a further lipid.

In one embodiment the further lipid is a second phosphatidylcholine.

In one embodiment the lipid particle is consisting of a shortened tetranectin-apolipoprotein A-I fusion protein as reported herein, two different phosphatidylcholines, and a detergent.

In one embodiment the phosphatidylcholine and the second phosphatidylcholine differ in one or two carboxylic acid moieties or carboxylic acid moiety derivatives which are esterified to the phosphoglycerol backbone of the phosphatidylcholine.

In one embodiment the phosphatidylcholine is POPC and the second phosphatidylcholine is DPPC.

In one embodiment the molar ratio of POPC to DPPC in the lipid particle is of from 99:1 to 1:99. In one embodiment the molar ratio of POPC to DPPC in the lipid particle is of from 99:1 to 10:90. In one embodiment the molar ratio of POPC to DPPC in the lipid particle is of from 99:1 to 25:75.

In one embodiment the shortened tetranectin-apolipoprotein A-I fusion protein as reported herein is non-covalently associated with the POPC and the DPPC.

In one embodiment the shortened tetranectin-apolipoprotein A-I fusion protein as reported herein is a multimer comprising three monomers.

In one embodiment the lipid particle comprises less than 0.75% by weight detergent. In one embodiment the detergent is a sugar-based detergent, or a polyoxyalkylene-based detergent, or a bile-salt based detergent, or a synthetic detergent, or a combination thereof. In one embodiment the detergent is cholic acid.

In one embodiment the lipid particle is capable of binding to a receptor selected from the group consisting of cubilin, Scavenger receptor class B, type 1 (SR-BI), ATP-binding cassette 1 (ABCA-1), Lecithin-cholesterol acyltransferase (LCAT), Cholesteryl-ester transfer protein (CETP), or Phospholipid transfer protein (PLTP).

In one embodiment the lipid particle according to the invention is characterized in that the number of phospholipid molecules per apolipoprotein monomer in the lipid particle is of from 40 to 120. In one embodiment the number of phospholipid molecules per apolipoprotein monomer in the lipid particle is of from 50 to 90.

In one embodiment the shortened tetranectin-apolipoprotein A-I fusion protein is recombinantly produced.

One aspect as reported herein is a pharmaceutical composition comprising a shortened tetranectin-apolipoprotein A-I fusion protein as reported herein or a lipid particle as reported herein.

One aspect as reported herein is a shortened tetranectin-apolipoprotein A-I fusion protein as reported herein or a lipid particle as reported herein for use as a medicament.

One aspect as reported herein is the use of a shortened tetranectin-apolipoprotein A-I fusion protein as reported herein or a lipid particle as reported herein for the manufacture of a medicament.

One aspect as reported herein is the use of a shortened tetranectin-apolipoprotein A-I fusion protein as reported herein or a lipid particle as reported herein for the manufacture of a medicament
for secondary prevention in patients with an acute coronary syndrome, or
for the prevention or treatment of atherosclerosis wherein a shortened tetranectin-apolipoprotein A-I fusion protein as reported herein or a lipid particle as reported herein is comprised in an amount sufficient to induce reverse cholesterol transport and/or plaques pacification in a subject, or
for inducing reverse cholesterol transport and/or plaques pacification, or
for cleaning/dissolution/stabilization of atherosclerotic plaques in blood vessels of a subject or for redistributing cholesterol from the wall of arteries to the liver of a subject, or
for preventing or treating a valvular stenosis in a subject, or
for increasing the number of HDL particles in a subject, or
for initiation of reverse cholesterol transport in a subject, or
for the removal of endotoxins, or
for the prevention of septic shock
for the treatment of angina pectoris, or
for the treatment of myocardial infarction, or
for the treatment of unstable angina pectoris, or
for the treatment of arterial stenoses such as peripheral artery diseases (PAD), carotis stenosis, cerebral arterial stenosis or coronary arterial stenosis, or
for the treatment of vascular demencia, or
for the treatment of amaurosis fugax.

One aspect as reported herein is the use of a shortened tetranectin-apolipoprotein A-I fusion protein as reported herein or a lipid particle as reported herein in the manufacture of a medicament.

One aspect as reported herein is a method for the manufacture of a medicament
for secondary prevention in patients with an acute coronary syndrome, or
for the prevention or treatment of atherosclerosis wherein a shortened tetranectin-apolipoprotein A-I fusion protein as reported herein or a lipid particle as reported herein is comprised in an amount sufficient to induce reverse cholesterol transport and/or plaques pacification in a subject, or
for inducing reverse cholesterol transport and/or plaques pacification, or for cleaning/dissolution/stabilization of atherosclerotic plaques in blood vessels of a subject or for redistributing cholesterol from the wall of arteries to the liver of a subject, or for preventing or treating a valvular stenosis in a subject, or
for increasing the number of HDL particles in a subject, or
for initiation of reverse cholesterol transport in a subject, or
for the removal of endotoxins, or
for the prevention of septic shock
for the treatment of angina pectoris, or
for the treatment of myocardial infarction, or
for the treatment of unstable angina pectoris, or
for the treatment of arterial stenoses such as peripheral artery diseases (PAD), carotis stenosis, cerebral arterial stenosis or coronary arterial stenosis, or
for the treatment of vascular demencia, or
for the treatment of amaurosis fugax.

One aspect as reported herein is a method for
secondary prevention in patients with an acute coronary syndrome, or
the prevention or treatment of atherosclerosis wherein a shortened tetranectin-apolipoprotein A-I fusion protein as reported herein or a lipid particle as reported herein is comprised in an amount sufficient to induce reverse cholesterol transport and/or plaques pacification in a subject, or
for inducing reverse cholesterol transport and/or plaques pacification, or
for cleaning/dissolution/stabilization of atherosclerotic plaques in blood vessels of a subject or for redistributing cholesterol from the wall of arteries to the liver of a subject, or
for preventing or treating a valvular stenosis in a subject, or
for increasing the number of HDL particles in a subject, or
for initiation of reverse cholesterol transport in a subject, or
for the removal of endotoxins, or
for the prevention of septic shock
for the treatment of angina pectoris, or
for the treatment of myocardial infarction, or
for the treatment of unstable angina pectoris, or
for the treatment of arterial stenoses such as peripheral artery diseases (PAD), carotis stenosis, cerebral arterial stenosis or coronary arterial stenosis, or
for the treatment of vascular demencia, or
for the treatment of amaurosis fugax.

One aspect as reported herein is a shortened tetranectin-apolipoprotein A-I fusion protein as reported herein or a lipid particle as reported herein for use in treating
acute coronary syndrome, or
atherosclerosis, or
atherosclerotic plaques in blood vessels of a subject, or
valvular stenosis in a subject, or
septic shock, or
angina pectoris, or
myocardial infarction, or
unstable angina pectoris, or
arterial stenoses, or
peripheral artery diseases (PAD), or
carotis stenosis, or
cerebral arterial stenosis, or
coronary arterial stenosis, or
vascular demencia, or
amaurosis fugax.

One aspects as reported herein is a shortened tetranectin-apolipoprotein A-I fusion protein as reported herein or a lipid particle as reported herein for use in inducing reverse cholesterol transport, or
inducing plaques pacification, or
cleaning or dissoluting or stabilizing atherosclerotic plaques, or
redistributing cholesterol from the wall of arteries to the liver, or
increasing the number of HDL particles, or
removal of endotoxins.

One aspect as reported herein is a method of treating an individual having acute coronary syndrome, or atherosclerosis, or atherosclerotic plaques in blood vessels, or valvular stenosis, or septic shock, or angina pectoris, or myocardial infarction, or unstable angina pectoris, or arterial stenoses, or peripheral artery diseases (PAD), or carotis stenosis, or cerebral arterial stenosis, or coronary arterial stenosis, or vascular demencia, or amaurosis fugax comprising administering to the individual an effective amount of a shortened tetranectin-apolipoprotein A-I fusion protein as reported herein or a lipid particle as reported herein.

One aspect as reported herein is a method of inducing reverse cholesterol transport, or inducing plaques pacification, or cleaning or dissoluting or stabilizing atherosclerotic plaques, or redistributing cholesterol from the wall of arteries to the liver, or increasing the number of HDL particles, or removing endotoxins in an individual comprising administering to the individual an effective amount of a shortened tetranectin-apolipoprotein A-I fusion protein as reported herein or a lipid particle as reported herein to induce reverse cholesterol transport, or to induce plaques pacification, or to clean or dissolute or stabilize atherosclerotic plaques, or to redistribute cholesterol from the wall of arteries to the liver, or to increase the number of HDL particles, or to remove endotoxins.

In one embodiment the non-normal lipid level is in a body fluid. In one embodiment the body fluid is whole blood or blood serum.

In one embodiment the non-normal lipid level is an increased cholesterol level.

In one embodiment the lipid containing deposition is a plaque in a blood vessel.

In one embodiment the disease is a cardiovascular disease.

One aspect as reported herein is a method of treating a disease or condition characterized by non-normal lipid levels or a lipid containing deposition within body components comprising
i) administering a therapeutically effective amount of a shortened tetranectin-apolipoprotein A-I fusion protein as reported herein or a lipid particle as reported herein to a subject in need of a treatment or an artificial system, and
ii) optionally monitoring the lipid level or the lipid containing deposition of a subject for a change.

One aspect as reported herein is a method for secondary prevention in patients with an acute coronary syndrome comprising administering to a subject in need thereof a shortened tetranectin-apolipoprotein A-I fusion protein as reported herein or a lipid particle as reported herein.

One aspect as reported herein is a diagnostic composition comprising a shortened tetranectin-apolipoprotein A-I fusion protein as reported herein or a lipid particle as reported herein wherein the apolipoprotein or the lipid particle is labeled allowing for the detection of the fusion protein or lipid particle within a sample or subject.

One aspect as reported herein is the use of a shortened tetranectin-apolipoprotein A-I fusion protein as reported herein or a lipid particle as reported herein for diagnosis.

One aspect as reported herein is the use of a shortened tetranectin-apolipoprotein A-I fusion protein as reported herein or a lipid particle as reported herein for the prevention or treatment of a subject suffering from a disease or condition characterized by the presence of a non-normal lipid level or a lipid containing deposition.

One aspect as reported herein is a nucleic acid encoding a shortened tetranectin-apolipoprotein A-I fusion protein as reported herein.

One aspect as reported herein is a cell comprising a nucleic acid as reported herein.

In one embodiment the cell is selected from the *E. coli* strains such as CSPZ-2, K12 strain 294 (ATCC 31446), B, X 1776 (ATCC 31537), W3110 (ATCC 273325), BL21, RM__82, SCS__110, G, XL-1_F-, SE__13009, LA__5709, C 600, CSH__1, TG__1, UT400, and UT5600.

One aspect as reported herein is a multimer comprising three shortened tetranectin-apolipoprotein A-I fusion protein as reported herein as monomers, wherein the monomers are not covalently bound to each other.

BRIEF DESCRIPTION OF THE FIGURES

FIG. 1. Results of in vivo rabbit studies conducted with five lipid particles differing in their lipid composition. Top: cholesterol mobilization and, thus, efficacy could be shown for all prepared batches. Bottom: Increase of liver enzyme was noticed for lipid particles generated by the use of DPPC as single phospholipid.

FIG. 12. Results of in vivo rabbit studies performed with tetranectin-apolipoprotein A-I lipidated with DMPC (1:100) (di myristoyl phosphatidylcholine) (a) and not lipidated in PBS (b).

FIG. 13. SE-HPLC chromatogram of lipid particles containing wild-type apolipoprotein A-I (A) and tetranectin-apolipoprotein A-I as reported herein (B) stored at 5° C. and 40° C.

DETAILED DESCRIPTION OF THE INVENTION

Definitions

Figure 2:
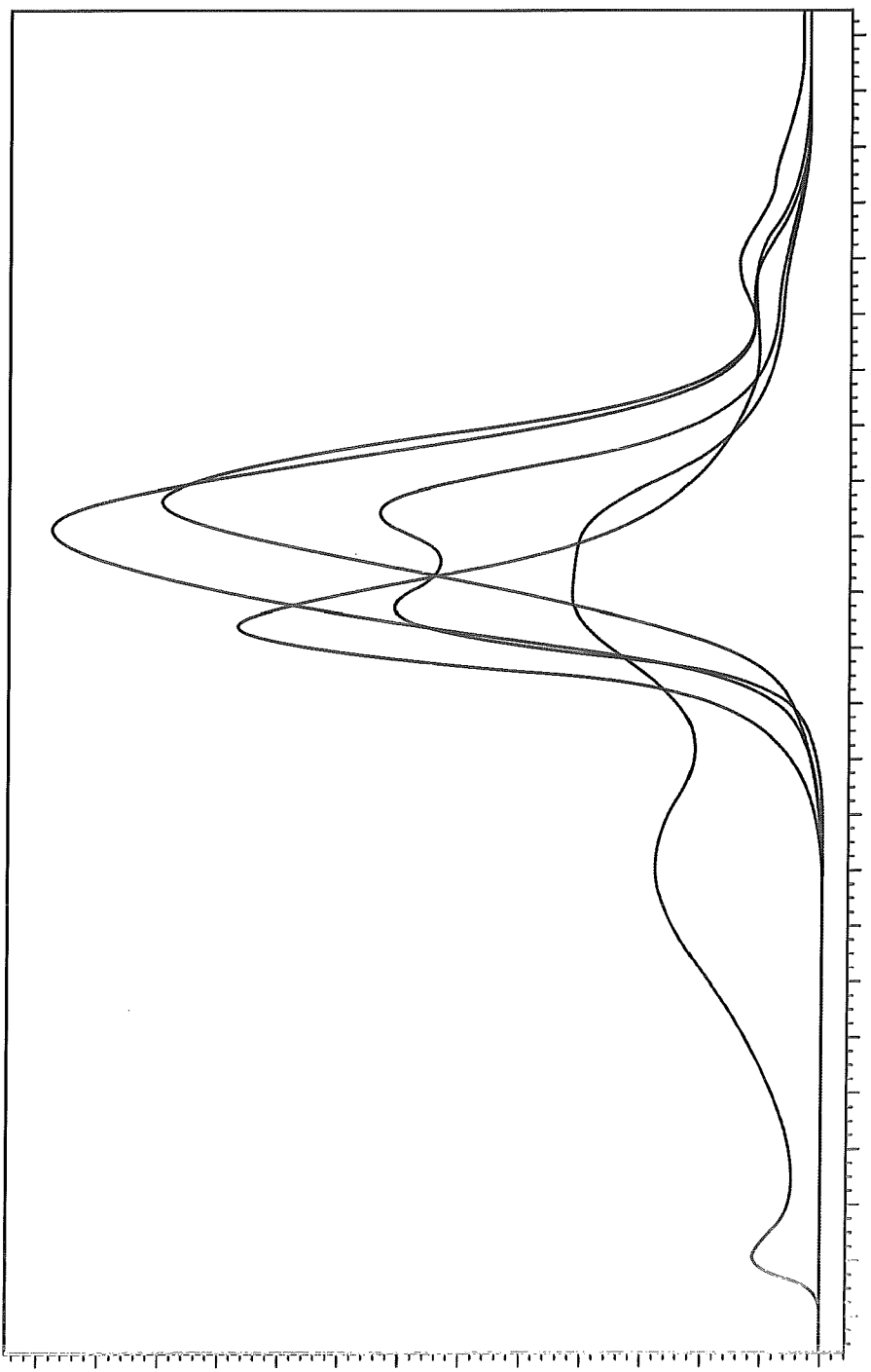
FIG. 2. SEC-MALLS analysis of lipid particles of POPC and apolipoprotein according to the current invention; molar ratios 1:20 to 1:160.

The term "apolipoprotein" denotes a protein that is comprised in a lipid or lipoprotein particle, respectively.

The term "apolipoprotein A-I" denotes an amphiphilic, helical polypeptide with protein-lipid and protein-protein interaction properties. Apolipoprotein A-I is synthesized by the liver and small intestine as prepro-apolipoprotein of 267 amino acid residues which is secreted as a pro-apolipoprotein that is cleaved to the mature polypeptide having 243 amino acid residues. Apolipoprotein A-I is consisting of 6 to 8 different amino acid repeats consisting each of 22 amino acid residues separated by a linker moiety which is often proline, and in some cases consists of a stretch made up of several residues. An exemplary human apolipoprotein A-I amino acid sequence is reported in GenPept database entry NM-000039 or database entry X00566; GenBank NP-000030.1 (gi 4557321). Of human apolipoprotein A-I (SEQ ID NO: 02) naturally occurring variants exist, such as P27H, P27R, P28R, R34L, G50R, L84R, D113E, A-A119D, D127N, deletion of K131, K131M, W132R, E133K, R151C (amino acid residue 151 is changed from Arg to Cys, apolipoprotein A-I-Paris), E160K, E163G, P167R, L168R, E171V, P189R, R197C (amino acid residue 173 is change from Arg to Cys, apolipoprotein A-I-Milano) and E222K. Also included are variants that have conservative amino acid modifications.

The term "cardiovascular disease" in general denotes a disease or condition with respect to heart or blood vessels, such as arteriosclerosis, coronary heart disease, cerebrovascular disease, aortoiliac disease, ischemic heart disease or peripheral vascular disease. Such a disease may not be discovered prior to an adverse event as a result of the disease, such as myocardial infarct, stroke, angina pectoris, transient ischemic attacks, congestive heart failure, aortic aneurysm, mostly resulting in death of the subject.

The term "cholate" denotes $3\alpha,7\alpha,12\alpha$-trihydroxy-$5\beta$-cholan-24-oic acid or a salt thereof, especially the sodium salt.

The term "critical micelle concentration" and its abbreviation "CMC", which can be used interchangeably, denote the concentration of surfactants or detergents above which individual detergent molecules (monomers) aggregate spontaneously to micelles (micelles, round rods, lamellar structures etc.).

The term "conservative amino acid modification" denotes modifications of the amino acid sequence which do not affect or alter the characteristics of the lipid particle or the apolipoprotein according to the invention. Modifications can be introduced by standard techniques known in the art, such as site-directed mutagenesis and PCR-mediated mutagenesis. Conservative amino acid modifications include ones in which the amino acid residue is replaced with an amino acid residue having a similar side chain. Families of amino acid residues having similar side chains have been defined in the art. These families include amino acids with basic side chains (e.g. lysine, arginine, histidine), acidic side chains (e.g. aspartic acid, glutamic acid), uncharged polar side chains (e.g. glycine, asparagine, glutamine, serine, threonine, tyrosine, cysteine, tryptophan), non-polar side chains (e.g. alanine, valine, leucine, isoleucine, proline, phenylalanine, methionine), beta-branched side chains (e.g. threonine, valine, isoleucine), and aromatic side chains (e.g. tyrosine, phenylalanine, tryptophan, histidine). A "variant" protein, refers therefore herein to a molecule which differs in amino acid sequence from a "parent" protein's amino acid sequence by up to ten, in one embodiment from about two to about five, additions, deletions, and/or substitutions Amino acid sequence modifications can be performed by mutagenesis based on molecular modeling as described by Riechmann, L., et al., Nature 332 (1988) 323-327, and Queen, C., et al., Proc. Natl. Acad. Sci. USA 86 (1989) 10029-10033.

The homology and identity of different amino acid sequences may be calculated using well known algorithms such as BLOSUM 30, BLOSUM 40, BLOSUM 45, BLOSUM 50, BLOSUM 55, BLOSUM 60, BLOSUM 62, BLOSUM 65, BLOSUM 70, BLOSUM 75, BLOSUM 80, BLOSUM 85, or BLOSUM 90. In one embodiment the algorithm is BLOSUM 30.

The formation of lipid particles may be performed by incubating the apolipoprotein with detergent solubilized lipids at their respective transition temperature. The term "detergent" denotes a surface active chemical substance. A "detergent" is generally an amphiphatic molecule with a non-polar, hydrophobic part and a polar, hydrophilic part. The term "zwitterionic detergent" denotes a surface active chemical compound that has overall zero charge and at the same time comprises at least one positively charged moiety and at least one negatively charged moiety. In one embodiment the detergent is selected from sugar-based detergents, polyoxyalkylene-based detergents, bile-salt based detergents, synthetic detergents or a combination thereof. The term "sugar-based detergent" denotes a detergent selected from n-octyl-beta-D-glucopyranoside, n-nonyl-beta-D-glucopyrano side, n-dodecyl-beta-D-maltopyranoside, or 5-cyclohexylpentyl-beta-D-maltopyranoside, and derivatives thereof. The term "bile-salt based detergent" denotes a detergent selected from sodium cholate, potassium cholate, lithium cholate, 3-[(3-chloramidopropyl) dimethylammonio]-yl-propane sulfonate (CHAPS), 3-[(3-chloramidopropyl) dimethylammonio]-2-hydroxyl propane sulfonate (CHAPSO), and derivatives thereof. The term "polyoxyalkylene-based detergent" denotes a detergent selected from Tween 20, Triton X-100, Pluronic F68, and a derivatives thereof. The term "synthetic detergents" denotes a detergent selected from Zwittergent 3-6, Zwittergent 3-8, Zwittergent 3-10, Zwittergent 3-12, and derivatives thereof.

An "effective amount" of an agent, e.g., a pharmaceutical formulation, refers to an amount effective, at dosages and for periods of time necessary, to achieve the desired therapeutic or prophylactic result.

The term "high density lipoprotein particle" or its abbreviation "HDL particle", which can be used interchangeably, denotes a lipid-protein-complex comprising as main proteinaceous compound apolipoprotein A-I.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The term "increase lipid efflux" and grammatical equivalents thereof denotes an increased level and/or rate of lipid efflux, promoting lipid efflux, enhancing lipid efflux, facilitating lipid efflux, upregulating lipid efflux, improving lipid efflux, and/or augmenting lipid efflux from cells or plaques. In one embodiment, the lipid efflux comprises efflux of phospholipid, triglyceride, cholesterol, and/or cholesterol ester.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

The term "DPPC" denotes the phospholipid 1,2-di-palmitoyl-sn-glycero-3-phosphatidylcholine also referred to as 1,2-dipalmitoyl-phosphatidylcholine.

The term "multimer" denotes a complex consisting of two or more monomers. A multimer is formed by non-covalent interactions between the monomers. Each monomer comprises a multimerization domain. In one embodiment the multimer comprises 2 or 3 monomers. In another embodiment the multimerization domains interact via non-covalent interactions between the individual multimerization domains comprised in each monomer. The term "multimerization domain" denotes amino acid sequences capable of covalently or non-covalently associating two or more monomeric molecules. A multimerization domain is capable of interacting with multimerization domains of different, similar, or identical amino acid sequence. In one embodiment the multimerization domain is the tetranectin trimerising structural element or a derivative thereof that has an amino acid sequence that is at least 68% identical with the consensus amino acid sequence of SEQ ID NO: 03. In one embodiment the cysteine residue at position 50 of SEQ ID NO: 03 is substituted by a different amino acid residue, in another embodiment by a serine residue, or a threonine residue, or a methionine residue. Polypeptides comprising a multimerization domain can associate with one or more other polypeptides also comprising a multimerization domain. The multimer formation can be initiated simply by mixing the polypeptides under suitable conditions. In another embodiment the multimerization domain has the amino acid sequence of SEQ ID NO: 03 wherein of from 1 to 10 residues have been deleted from or added to the N- or C-terminus of the amino acid sequence. In a further embodiment the multimerization domain has an amino acid sequence of SEQ ID NO: 03 wherein six or nine amino acid residues have been deleted from the N-terminus of the amino acid sequence. In still another embodiment the multimerization domain has an amino acid sequence of SEQ ID NO: 03 wherein the N-terminal amino acid residue L or the N-terminal amino acid residues C and L have been deleted. In one embodiment the multimerization domain is the tetranectin trimerising structural element and has the amino acid sequence of SEQ ID NO: 03. The multimer is in one embodiment a homomer.

The multimers may be homomers or heteromers, since different apolipoproteins comprising a multimerization domain can be combined to be incorporated into the multimer. In one embodiment the multimer is a trimeric homomer.

According to one embodiment the multimerization domain is obtained from tetranectin. In one embodiment the multimerization domain comprises the tetranectin trimerising structural element that has an amino acid sequence of SEQ ID NO: 04. The trimerising effect of the tetranectin trimerising structural element is caused by a coiled coil structure which interacts with the coiled coil structure of two other tetranectin trimerising structural elements to form a trimer. The tetranectin trimerising structural element may be obtained from human tetranectin, from rabbit tetranectin, from murine tetranectin, or from C-type lectin of shark cartilage. In one embodiment the tetranectin trimerising structural element comprises a sequence having at least 68%, or at least 75%, or at least 81%, or at least 87%, or at least 92% identity with the consensus sequence of SEQ ID NO: 03.

The term "non-covalent interactions" denotes non-covalent binding forces such as ionic interaction forces (e.g. salt bridges), non-ionic interaction forces (e.g. hydrogen-bonds), or hydrophobic interaction forces (e.g. van-der-Waals forces or n-stacking interactions).

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "phosphatidylcholine" denotes a molecule consisting of one glycerol moiety, two carboxylic acid moieties and one phosphocholine moiety, wherein the glycerol moiety is covalently bound to the other moieties each by a ester bond, i.e. two carboxylic ester bonds and one phosphoric ester bond, whereby the phosphoric ester bond is either to the 1-hydroxyl group or the 3-hydroxyl group of the glycerol moiety. The term "carboxylic acid moiety" denotes an organic moiety comprising at least one acyl group (R—C(O) O). The phosphatidylcholine may be of any kind or source. In one embodiment the phosphatidylcholine is selected from egg phosphatidylcholine, soybean phosphatidylcholine, dipalmitoyl phosphatidylcholine, dimyristoyl phosphatidylcholine, distearoyl phosphatidylcholine, dilauryl phosphatidylcholine, dipalmitoyl phosphatidylcholine, 1-myristoyl-2-palmitoyl phosphatidylcholine, 1-palmitoyl-2-myristoyl phosphatidylcholine, 1-palmitoyl-2-stearoyl phosphatidylcholine, 1-stearoyl-2-palmitoyl phosphatidylcholine, dioleoyl phosphatidylcholine, 1-palmitoyl-2-oleoyl phosphatidylcholine, 1-oleoyl-2-palmitoyl phosphatidylcholine, and an analogues and derivatives thereof.

All phospholipids as used herein may be derived from any source, i.e. (where appropriate) from soybean, milk, egg or even inner organs of animals excluding humans, they may be derived from natural origin, or semi-synthetic or even fully synthetic.

The term "POPC" denotes the phospholipid 1-palmitoyl-2-oleoyl-sn-glycero-3-phosphatidylcholine also referred to as 1-palmitoyl-2-oleoyl-phosphatidylcholine.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variant" includes also variants of an apolipoprotein or an apolipoprotein mimic as reported herein wherein in the variants the amino acid sequence of the respective apolipoprotein or apolipoprotein mimic comprises one or more amino acid substitution, addition or deletion. The modification may increase or decrease the affinity of the apolipoprotein for an apolipoprotein receptor or an apolipoprotein converting enzyme, or may increase the stability of the apolipoprotein variant compared to the respective apolipoprotein, or may increase the solubility of the apolipoprotein variant compared to the respective apolipoprotein in aqueous solutions, or may increase the recombinant production of the apolipoprotein variant compared to the respective apolipoprotein in/by host cells.

Shortened Tetranectin-Apolipoprotein A-I Fusion Protein

Herein is reported a shortened tetranectin-apolipoprotein A-I fusion protein.

The shortened tetranectin-apolipoprotein A-I fusion protein is a fusion protein of a N-terminally shortened human tetranectin trimerising structural element and the wild-type human apolipoprotein A-I. The amino acid sequence of the human tetranectin part is shortened by the first 9 amino acids, thus, starting with the isoleucine residue of position 10 and extended by the N-terminal amino acid residue proline. As a consequence of this truncation the naturally occurring O-glycosylation site at threonine residue of position 4 has been deleted. Between the tetranectin trimerising structural element and the human apolipoprotein A-I the five amino acid residues "SLKGS" (SEQ ID NO: 05) were removed.

The shortened tetranectin-apolipoprotein A-I fusion protein can have the amino acid sequence of SEQ ID NO: 01, or is a variant thereof with at least 70% sequence identity.

The tetranectin trimerising structural element provides for a domain that allows for the formation of a trimeric shortened tetranectin-apolipoprotein A-I fusion protein comprising multimer that is constituted by non-covalent interactions between each of the individual monomers.

In one embodiment the wild-type human apolipoprotein A-I can be a variant comprising conservative amino acid substitutions.

Apolipoprotein A-I can be determined enzymatically, via NMR spectroscopy, or by using monoclonal or polyclonal anti-apolipoprotein-A-I antibodies. Other aspects as reported herein are therefore polyclonal and monoclonal antibodies specifically binding the shortened tetranectin-apolipoprotein A-I fusion protein as reported herein. Such antibodies can be obtained with methods known to a person skilled in the art. Also the labeling of the fusion protein, a lipid particle comprising the fusion protein, and antibodies binding to the fusion protein or the lipid particle for use in immunoassays can be performed with methods known to a person of skill in the art.

In one embodiment the wild-type human apolipoprotein A-I is a variant comprising one to ten conservative amino acid substitutions.

Thus, in one embodiment the shortened tetranectin-apolipoprotein A-I fusion protein has the amino acid sequence of

```
                                         (SEQ ID NO: 01)
PIVNAKKDVVNTKMFEELKSRLDTLAQEVALLKEQQALQTVDEPPQSPWD

RVKDLATVYVDVLKDSGRDYVSQFEGSALGKQLNLKLLDNWDSVTSTFSK

LREQLGPVTQEFWDNLEKETEGLRQEMSKDLEEVKAKVQPYLDDFQKKWQ

EEMELYRQKVEPLRAELQEGARQKLHELQEKLSPLGEEMRDRARAHVDAL

RTHLAPYSDELRQRLAARLEALKENGGARLAEYHAKATEHLSTLSEKAKP

ALEDLRQGLLPVLESFKVSFLSALEEYTKKLNTQ.
```

The shortened tetranectin-apolipoprotein A-I fusion protein that has an amino acid sequence of SEQ ID NO: 01 is obtained with less side products as fusion proteins that have e.g. one additional N-terminal amino acid. This is shown in the following Table.

TABLE

| amino acid sequence of fusion protein starts with | main product (starts with amino acid sequence/ fraction) | by-product 1 (starts with amino acid sequence/ fraction) | by-product 2 (starts with amino acid sequence/ fraction) |
| --- | --- | --- | --- |
| APIVN | MAPIVN/60% | PIVN/39% | APIVN/1% |
| PIVN | PIVN/>90% | n.d. | n.d. |

Sequence key: PIVN (amino acid residues 1-4 of SEQ ID NO: 1); APIVN (SEQ ID NO: 6); and MAPIVN (SEQ ID NO: 7).

If the shortened tetranectin-apolipoprotein A-I fusion protein is produced in *E. coli* it is obtained from inclusion bodies.

Lipid Particle

Herein is reported a lipid particle comprising a shortened tetranectin-apolipoprotein A-I fusion protein as reported herein.

In one embodiment the lipid particle comprises
a) a shortened tetranectin-apolipoprotein A-I fusion protein as reported herein,
b) a phosphatidylcholine, and
c) a further lipid.

In one embodiment the lipid particle comprises a shortened tetranectin-apolipoprotein A-I fusion protein as reported herein, a first phosphatidylcholine and a second phosphatidylcholine. In one embodiment the first phosphatidylcholine and the second phosphatidylcholine differ in one or two carboxylic acid moieties or carboxylic acid moiety derivatives esterified to the phospho-glycerol backbone of the phosphatidylcholine. In one embodiment the first phosphatidylcholine is POPC and the second phosphatidylcholine is DPPC.

In one embodiment the shortened tetranectin-apolipoprotein A-I fusion protein, the phosphatidylcholine, and the further lipid in the lipid particle are non-covalently associated.

The choice of the combination of lipids determines the efficacy and liver safety of lipid particles comprising apolipoprotein. In in vivo studies of DMPC containing lipid particles using rabbits it has been found that rabbits treated with 30 mg/kg showed severe side effects but survived whereas rabbits treated with 100 mg/kg died.

In vitro functional tests confirmed that a lipid particle containing a single phosphatidylcholine such as DPPC or POPC activate LCAT.

It was also shown that cholesterol efflux was higher when the lipid particle comprised a combination of different phospholipids. In the following Table the results obtained with phospholipid combinations differing in their lipid composition prepared for in vivo rabbit studies are shown.

TABLE

| phospholipid molar ratio used for producing the lipid particle | LCAT substrate | cholesterol efflux |
| --- | --- | --- |
| POPC | yes | yes |
| POPC:DPPC 3:1 | yes | yes |
| POPC:DPPC 1:1 | yes | yes |
| POPC:DPPC 1:3 | no | yes |
| DPPC | no | yes |

These results were also confirmed by in vivo data demonstrating cholesterol mobilization for all combinations. However, for lipid particles containing only the single phosphatidylcholine DPPC or the combination of DPPC and sphingomyelin (SM) an increase in liver enzymes was determined (FIG. 1).

From the technical point of view the formation of lipid particles with pure DPPC is more convenient compared to the formation with pure POPC. The risk of precipitate formation is reduced by using a combination of different phospholipids. Also the phase transition temperature of 41° C. for pure DPPC makes it easier to prepare the lipid particle compared to pure POPC that has a phase transition temperature of 4° C. Also the obtained product is more homogeneous. This can be confirmed by lipid particle analysis via SEC-MALLS, an analytical tool which also allows the determination of the protein-lipid composition (protein-conjugate analysis). In FIG. 2 a chromatogram of samples resolved in a size-exclusion chromatography (UV280 detection) is shown. An inhomogeniety of a sample can be seen by the occurrence of multiple separated or semi-detached peaks.

The number of POPC molecules per apolipoprotein monomer in the lipid particle when pure POPC is used for producing the lipid particle is in one embodiment of from 40 to 85, in one embodiment of from 50 to 80, and in one embodiment of from 54 to 75.

The number of DPPC molecules per apolipoprotein monomer in the lipid particle when pure DPPC is used for producing the lipid particle is in one embodiment of from 50 to 150, in one embodiment of from 65 to 135, in one embodiment of from 76 to 123, and in one embodiment of from 86 to 102.

The number of phospholipid molecules per apolipoprotein monomer in the lipid particle when a mixture of POPC and DPPC at a molar ratio of 1:3 is used for producing the lipid particle is in one embodiment of from about 50 to about 120, in one embodiment of from about 65 to about 105, and in one embodiment of from about 72 to about 96.

The number of lipid molecules per apolipoprotein monomer in the lipid particle when a mixture of POPC and DPPC at a molar ratio of 1:1 is used for producing the lipid particle is in one embodiment of from 50 to 120, in one embodiment of from 60 to 100, and in one embodiment of from 71 to 92.

The number of lipid molecules per apolipoprotein monomer in the lipid particle when a mixture of POPC and DPPC at a molar ratio of 3:1 is used for producing the lipid particle is in one embodiment of from 50 to 90. In one embodiment the number is of from 60 to 90. In one embodiment the number is of from 60 to 88. In one embodiment the number is of from 60 to 80.

For the production of a lipid particle comprising apolipoprotein and POPC a molar ratio of apolipoprotein to POPC in one embodiment of from 1:40 to 1:100 is employed, in one embodiment a molar ratio of from 1:40 to 1:80 is employed, and in one embodiment a molar ratio of about 1:60 is employed.

For the production of a lipid particle comprising apolipoprotein and DPPC a molar ratio of apolipoprotein to DPPC in one embodiment of from 1:70 to 1:100 is employed, in one embodiment a molar ratio of from 1:80 to 1:90 is employed, and in one embodiment a molar ratio of about 1:80 is employed.

For the production of a lipid particle comprising apolipoprotein, POPC and DPPC a molar ratio of apolipoprotein to POPC and DPPC with POPC and DPPC at a 1:3 molar ratio in one embodiment of from 1:60 to 1:100 is employed, in one embodiment a molar ratio of from 1:70 to 1:90 is employed, and in one embodiment a molar ratio of about 1:80 is employed.

For the production of a lipid particle comprising apolipoprotein, DPPC and POPC the molar ratio of apolipoprotein to POPC and DPPC with POPC and DPPC at a 1:1 molar ratio is in one embodiment of from 1:60 to 1:100, in one embodiment the molar ratio is of from 1:60 to 1:80, and in one embodiment the molar ratio is about 1:70.

For the production of a lipid particle comprising apolipoprotein, DPPC and POPC in one embodiment a molar ratio of apolipoprotein to POPC and DPPC, whereby POPC and DPPC are at a 3:1 molar ratio, of from 1:50 to 1:100 is employed. In one embodiment a molar ratio of from 1:50 to 1:70 is employed. In one embodiment a molar ratio of about 1:60 is employed.

In one embodiment if a mixture of lipids is used for producing the lipid particle the mixture has a phase transition temperature of from 4° C. to 45° C., in one embodiment of from 10° C. to 38° C., and in one embodiment of from 15° C. to 35° C.

The lipid particle comprises in one embodiment an average number of from 1 to 10 fusion protein molecules per lipid particle, in one embodiment of from 1 to 8 fusion protein molecules per lipid particle, and in one embodiment of from 1 to 4 fusion protein molecules per lipid particle.

In one embodiment the lipid particle comprises an average number of at least 1, or 2, or 3, or 4, or 5, or 6, or 7, or 8, or 9, or 10 fusion protein molecules per lipid particle. In one embodiment the average number is 1.

In one embodiment the lipid particle comprises one or more further polypeptides beside the fusion protein.

Without limitation the lipid particle may serve as an enzymatic co-factor and/or a carrier for taking up lipids, especially cholesterol.

One or more detergents can be present in the lipid particle as reported herein. Such detergent can be any detergent, i.e. a pharmaceutically acceptable detergent or other detergents at non-toxic concentrations, such as a non-ionic or ionic detergent. The non-ionic detergent can be an alkylene oxide derivative of an organic compound which contains one or more hydroxyl groups.

In one embodiment the non-ionic detergent is selected from ethoxylated and/or propoxylated alcohol, or ester compounds, or mixtures thereof. In one embodiment the ester is selected from esters of sorbitol and fatty acids, such as sorbitan monooleate or sorbitan monopalmitate, oily sucrose esters, polyoxyethylene sorbitane fatty acid esters, polyoxyethylene sorbitol fatty acid esters, polyoxyethylene fatty acid esters, polyoxyethylene alkyl ethers, polyoxyethylene sterol ethers, polyoxyethylene-polypropoxy alkyl ethers, block polymers and cethyl ether, polyoxyethylene castor oil or hydrogenated castor oil derivatives and polyglycerine fatty acid esters.

In one embodiment the non-ionic detergent is selected from Pluronic®, Poloxamer®, Span®, Tween®, Polysorbate®, Tyloxapol®, Emulphor®, or Cremophor®.

The ionic detergent can be a bile duct agent. In one embodiment the ionic detergent is selected from cholic acid or deoxycholic acid, or their salts and derivatives, or from free fatty acids, such as oleic acid, linoleic acid and others.

In one embodiment the ionic detergent is selected from cationic lipids like $C_{10}$-$C_{24}$ alkylamine or alkanolamine and cationic cholesterol esters.

In one embodiment the lipid particle comprises less than 0.75% by weight detergent.

In one embodiment the lipid particle comprises less than 0.3% by weight detergent.

In one embodiment the detergent is selected from sugar-based detergents, polyoxyalkylene-based detergents, bile-salt based detergents, synthetic detergents, or a combination thereof. In one embodiment the detergent is cholic acid.

Properties:

The shortened tetranectin-apolipoprotein A-I fusion protein as reported herein or the lipid particle as reported herein can be used for the treatment and/or diagnosis of a disease or condition characterized by non-normal lipid levels or a deposition of lipids within body components, such as plaques in blood vessels.

Figure 3:
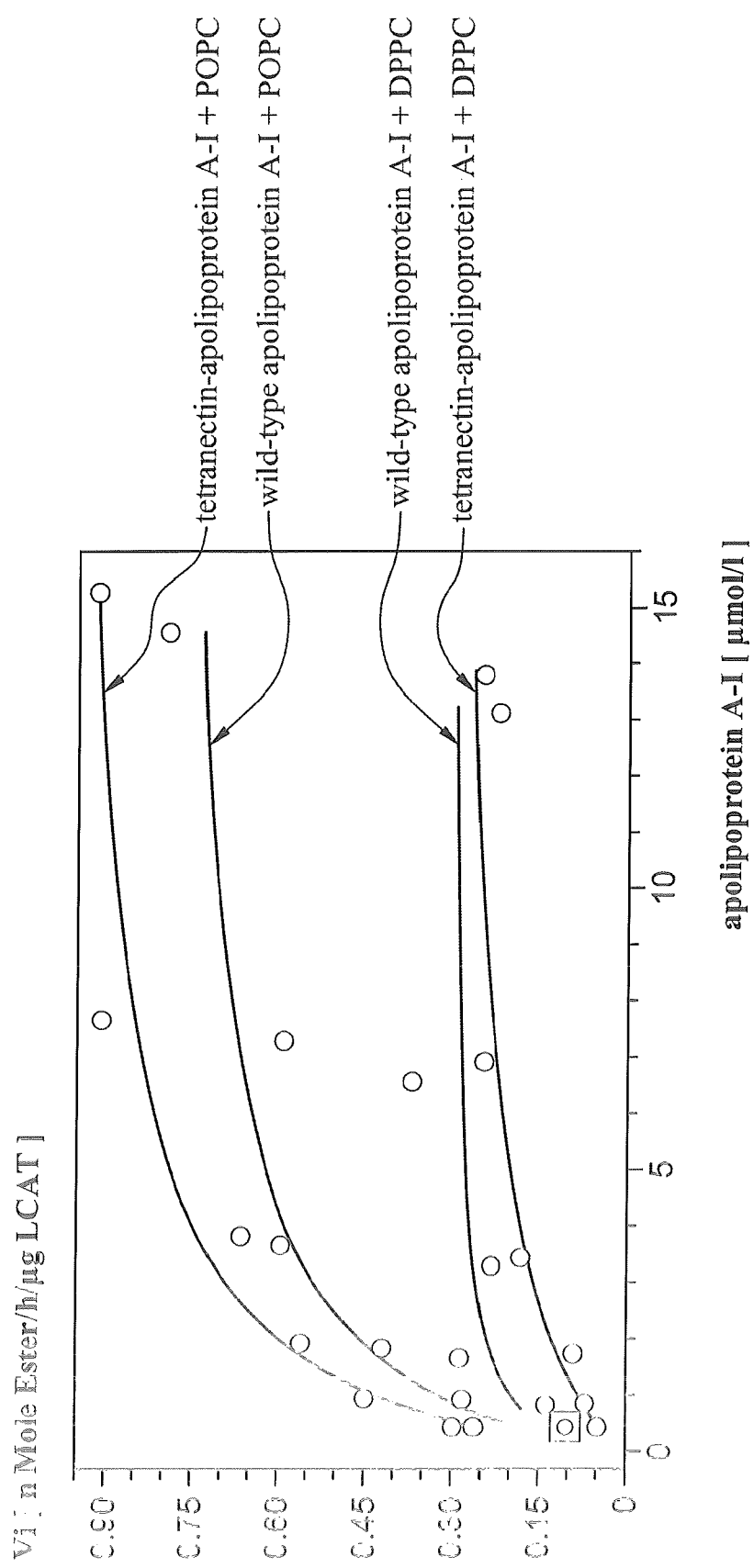
FIG. 3. Impact of DPPC and POPC on LCAT activity.

In order to determine the capacity of the lipid particle as reported herein to support LCAT catalyzed cholesterol esterification cholesterol can be incorporated in the lipid particle by addition of an ethanolic cholesterol solution. Lipid particles containing pure POPC are better LCAT substrates than complexes containing DPPC independent of their apolipoprotein constituent, such as wild-type apolipoprotein A-I or tetranectin-apolipoprotein A-I (FIG. 3).

Initial velocities of cholesterol esterification in lipid particles comprising different mixtures of POPC and DPPC show that mixtures are better LCAT substrates than a single pure phosphatidylcholine. This can be seen from the initial velocities of cholesterol esterification (see following Table and FIG. 4).

TABLE

| phospholipid molar ratio used for producing the lipid particle | $K_m$ [µM] | $V_{max}$ [nmol ester/h/µg LCAT] |
|---|---|---|
| POPC | 4.6 | 1.6 |
| POPC:DPPC 3:1 | 0.4 | 1.9 |
| POPC:DPPC 1:1 | 0.5 | 1.8 |
| POPC:DPPC 1:3 | 1.0 | 1.7 |
| DPPC | 0.9 | 1.8 |

Macrophage like human THP1 cells obtained by exposing THP-1 monocytic leukemia cells to phorbol myristate acetate and loaded with a radioactive labeled cholesterol tracer can be exposed to cholesterol acceptor test compounds.

Efflux velocity induced by acceptor test compounds can be calculated as the ratio of cholesterol radioactivity in the supernatant to the sum of the radioactivity in the cells plus their supernatant and compared to cells exposed to medium containing no acceptors and analyzed by linear fit. Parallel experiments can be performed using cells exposed and not exposed to a RXR-LXR agonist which is known to upregulate mainly ABCA-1 and bias efflux toward ABCA-1 mediated transport.

Figure 5:
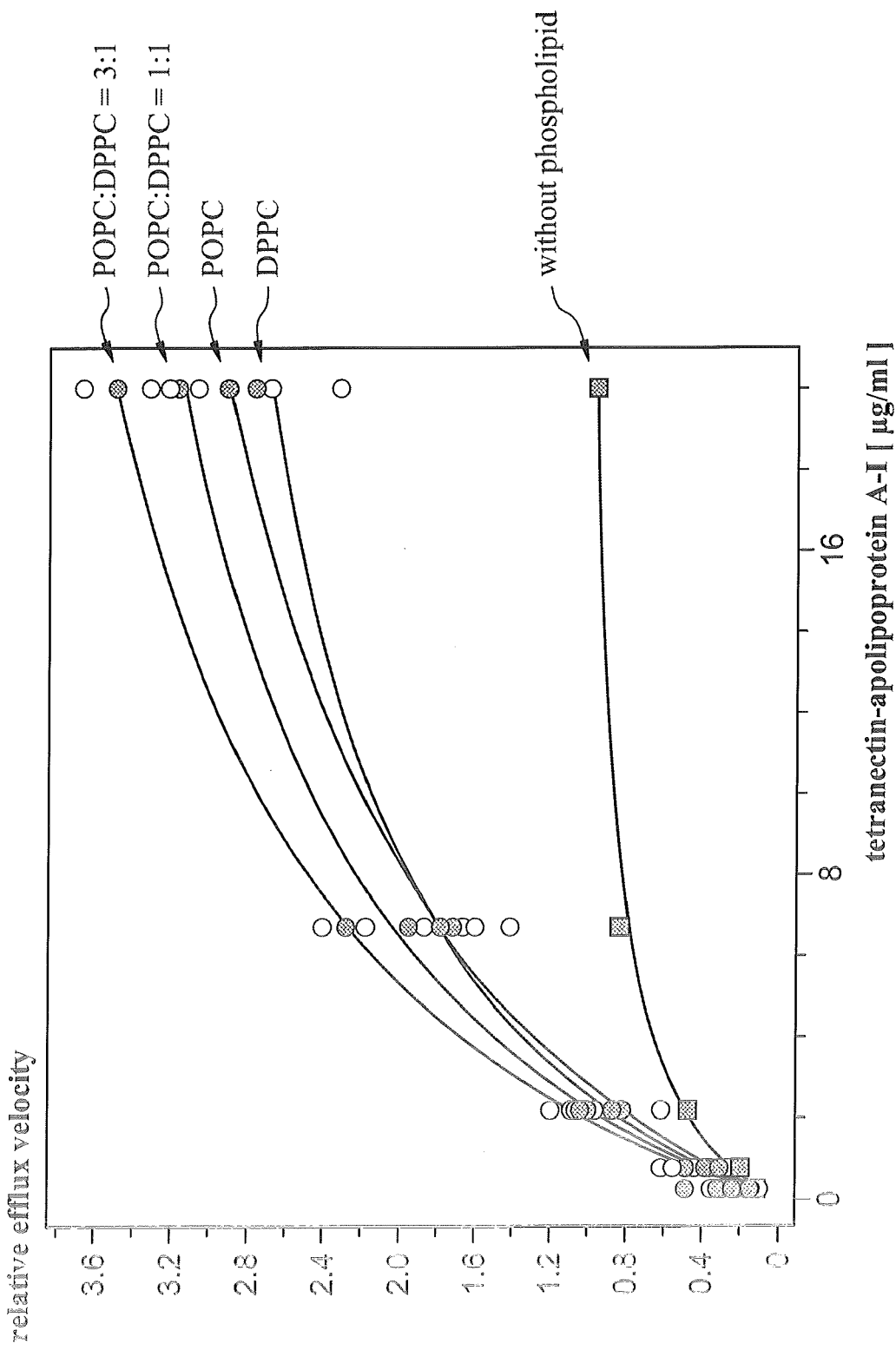
FIG. 5. Cholesterol efflux to THP-1 derived foam cells in cells not primed with a RXR-LXR agonist.
Figure 6:
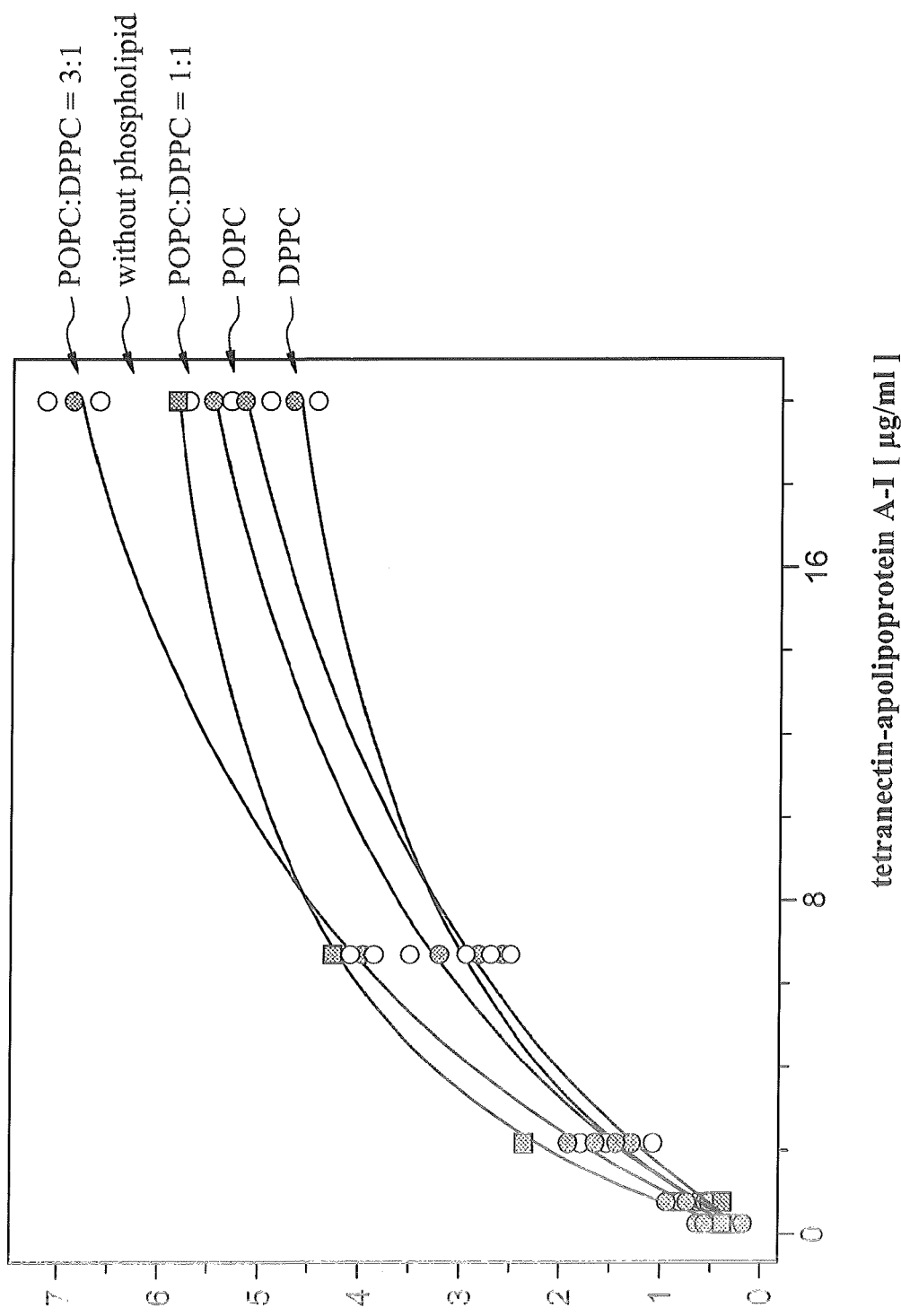
FIG. 6. Cholesterol efflux to THP-1 derived foam cells after ABCA-I pathway activation using an RXR-LXR agonist.
Figure 7:
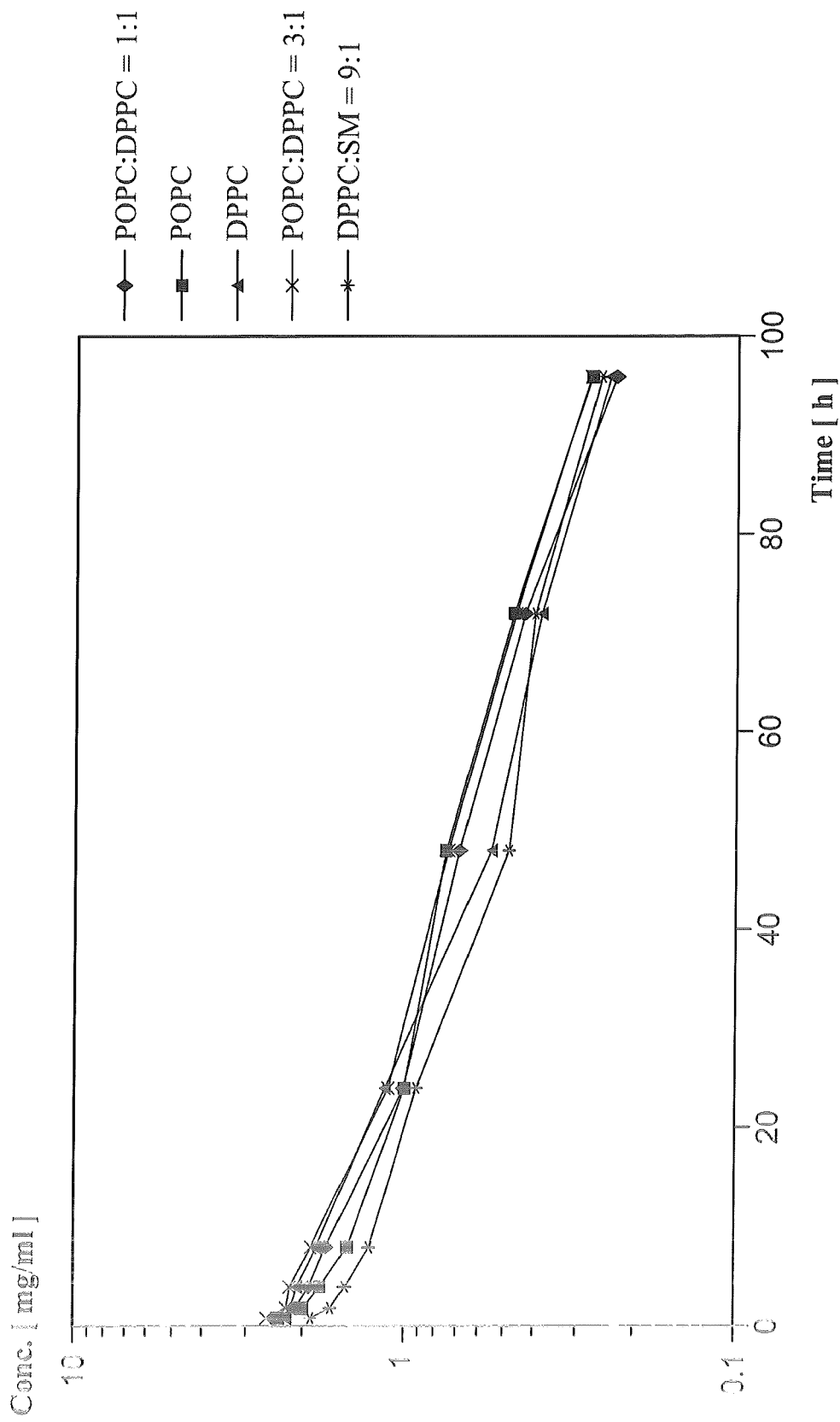
FIG. 7. Time dependent plasma concentration of different apolipoprotein compositions.

In cells not pre-treated with RXR-LXR lipid particles a higher increase in cholesterol efflux compared to the efflux obtained with non lipidated tetranectin-apolipoprotein A-I can be seen. Only a small influence of the lipid mixture on efflux can be observed in the tested series (FIG. 5). In cells pre-treated with RXR-LXR a comparable increase in cholesterol efflux can be seen using a non-lipidated tetranectin-apolipoprotein A-I. The overall increase was higher as compared to that observed with not pre-treated cells. Only a small influence of the lipid mixture on efflux can be observed in the tested series (FIG. 6).

all tested lipid particles comprising an initial distribution phase followed by log-linear decline of plasma concentrations (FIG. 7). As can be seen from the following Table pharmacokinetic parameters are similar for all tested compounds. The observed half-lives are close to 1.5 days.

TABLE

| phospholipid molar ratio used for producing the lipid particle | $C_L$ [ml/h/kg] | $V_{ss}$ [ml/kg] | $T_{1/2}$ [h] | $C_{max}$ [mg/ml] |
|---|---|---|---|---|
| POPC | 0.89 ± 0.22 | 45.0 ± 2.5 | 36.9 ± 8.2 | 2.40 ± 0.19 |
| POPC:DPPC 3:1 | 0.82 ± 0.06 | 37.8 ± 5.6 | 34.2 ± 4.5 | 2.65 ± 0.28 |
| POPC:DPPC 1:1 | 0.85 ± 0.14 | 43.1 ± 5.9 | 38.6 ± 10.6 | 2.34 ± 0.31 |
| DPPC | 0.96 ± 0.10 | 37.8 ± 4.9 | 30.2 ± 7.7 | 2.29 ± 0.19 |
| DPPC:SM 9:1 | 1.28 ± 0.62 | 50.7 ± 8.7 | 31.3 ± 8.2 | 1.91 ± 0.33 |

Figure 8:
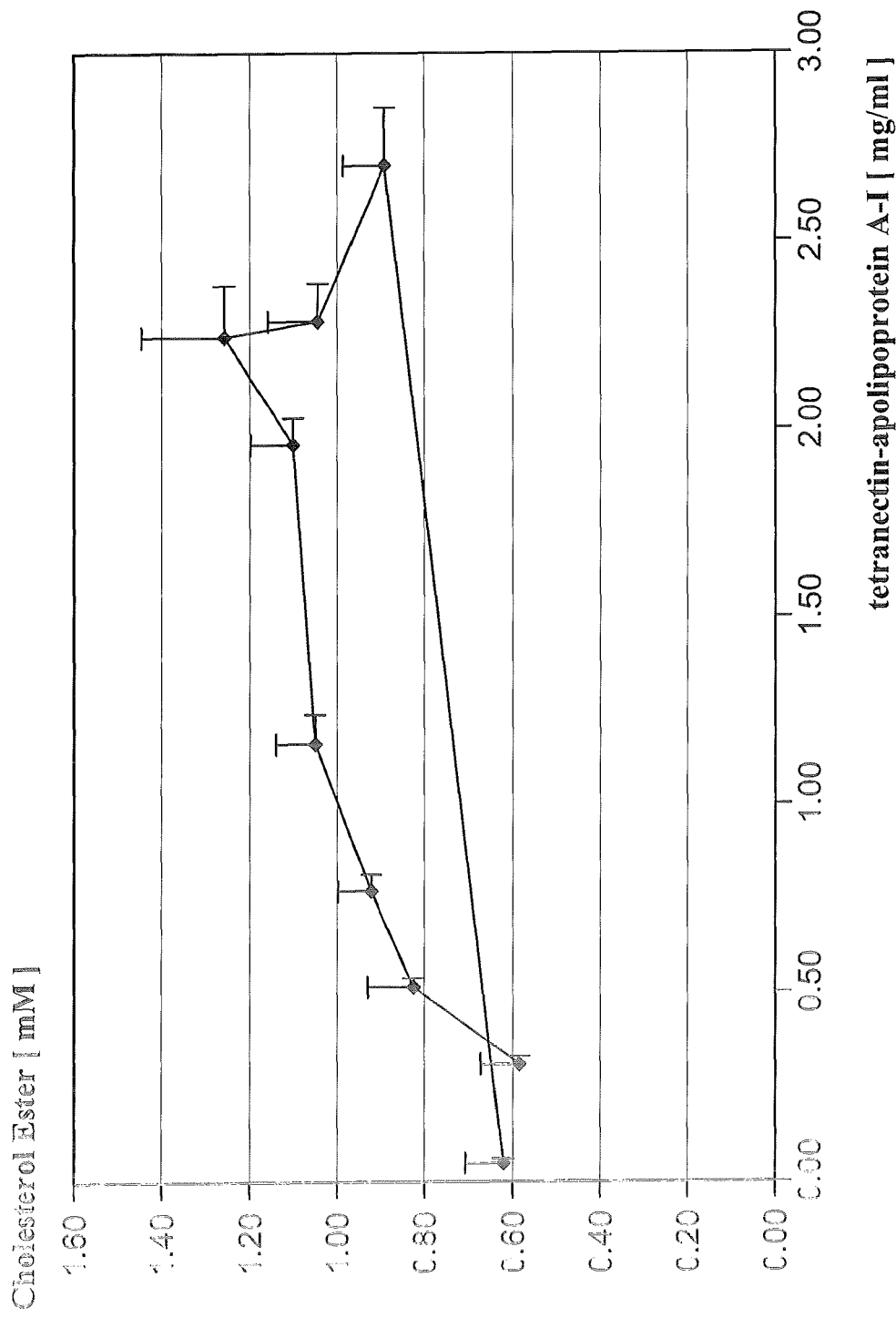
FIG. 8. Time and concentration course of cholesterol mobilization and esterification in plasma.

As can be seen from FIG. 8 cholesterol is mobilized and esterified in plasma. Plasma cholesterol ester levels do continue to increase even after the concentration of tetranectin-apolipoprotein A-I is already decreasing. When plasma tetranectin-apolipoprotein A-I levels have decreased to about 0.5 mg/ml (about 50% of normal wild-type apolipoprotein A-I) increased cholesterol ester levels can still be detected.

Figure 9:
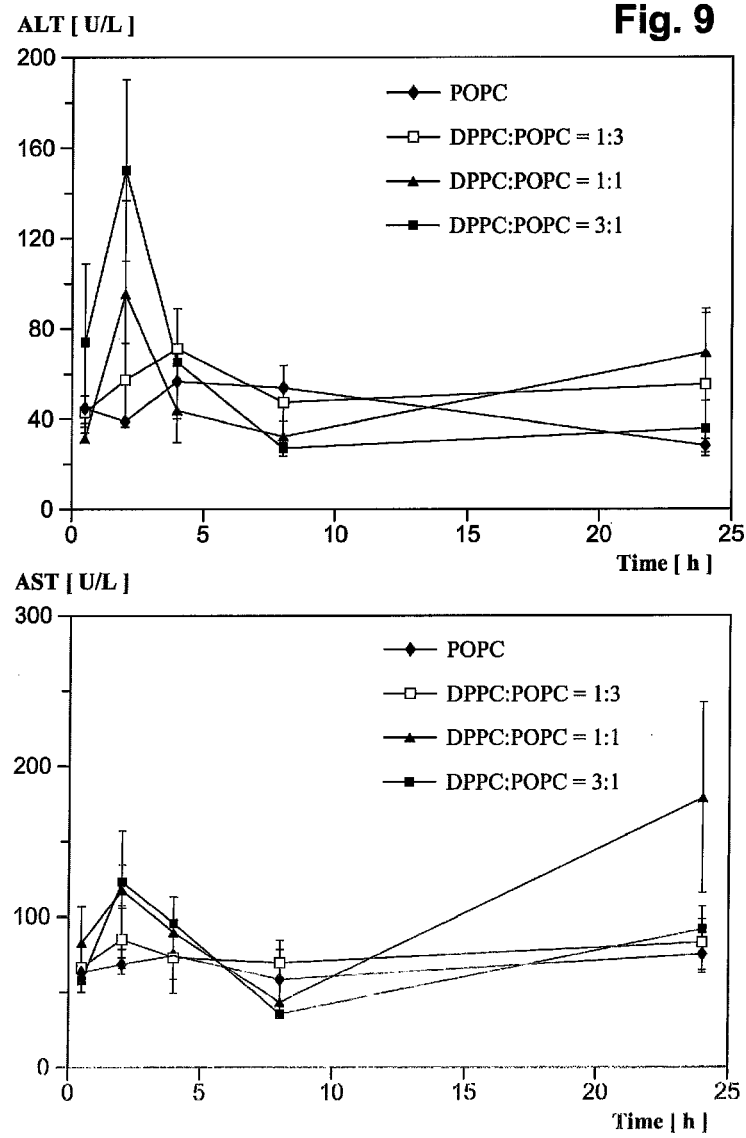
FIG. 9. Comparison of liver enzyme release (top panel=ALT, bottom panel=AST) by different compositions comprising apolipoprotein according to the invention in mice after a single i.v. injection of 100 mg/kg.
Figure 10:
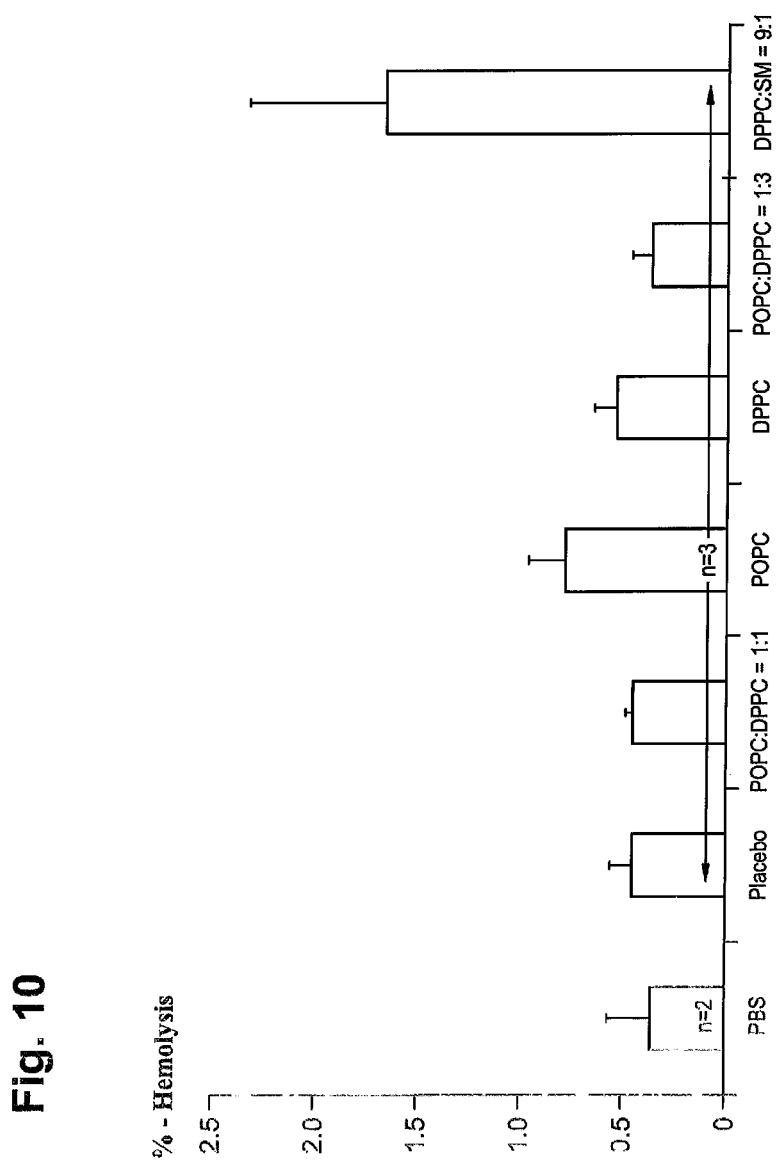
FIG. 10. In vivo rabbit study—spontaneous hemolysis in plasma.

Lipid particles comprising tetranectin-apolipoprotein A-I do not induced liver enzymes in rabbits as well as in mice as can be seen from FIGS. 1 and 9. Also no hemolysis can be determined in plasma samples obtained two hours after intravenous application (FIG. 10).

Therefore aspects as reported herein are a pharmaceutical composition and a diagnostic composition comprising a shortened tetranectin-apolipoprotein A-I fusion protein as reported herein or a lipid particle as reported herein.

The lipid particle as reported herein has improved in vivo properties compared to non-lipidated apolipoprotein and other lipid particles as shown in the following Table.

TABLE

| protein | lipid particle comprising | applied to | highest applied dose | acute liver toxicological effect | reference |
|---|---|---|---|---|---|
| apolipoprotein A-I mutants | no particle | rat | orally, 1 g/kg | no toxic effect up to 500 mg/kg | US 2005/0287636 |
| A-I, tetranectin-apolipoprotein A-I | DMPC | mouse | i.v. 1 to 1.2 mg/mouse | not described | WO 2002/38609; Graversen(2008) |
| pro apolipoprotein A-I | SM | not reported | not reported | injection, toxic at dose of 200 mg/kg | WO 2003/096983 |
| apolipoprotein A-I | PG/SM | rabbit | i.v. 15 mg/kg | not described | WO 2006/100567 |
| apolipoprotein A-I | PC (soybean) | human | 80 mg/kg | treatment group was discontinued early because of liver function test abnormalities (10-fold increase in alanine aminotransferase) | WO 2007/137400 |
| apolipoprotein A-I Milano variant | POPC | human | 45 mg/kg | one patient withdrawn due to development of an elevated aspartate aminotransferase level (3× upper limit of normal) | Nissen, S. E., et al., JAMA 290 (2003) 2292-2300 |
| tetranectin-apolipoprotein A-I | DMPC | rabbit | 100 mg/kg | lethal after 3-4 hours in all animals tested | |
| tetranectin-apolipoprotein A-I | POPC/DPPC | rabbit | 100 mg/kg | increase not observed | |
| tetranectin-apolipoprotein A-I | POPC/DPPC | rat | i.v. 500 mg/kg | increase not observed | |
| tetranectin-apolipoprotein A-I | POPC/DPPC | cynomolgus monkey | i.v. 200 mg/kg | increase not observed | |

Different lipid particles were tested in vivo in rabbits. The lipid particle was applied as intravenous infusion and serial blood sampling was performed over 96 h after application. Values of liver enzymes, cholesterol, and cholesterol ester were determined. Plasma concentrations are comparable for The efficiency at which cholesterol is mobilized into the blood can be determined by comparing the respective excursion of total cholesterol with apolipoprotein concentrations after administration of apolipoprotein in vivo. For a quantitative assessment, the quotient of the baseline corrected area under the concentration-time curve (AUC) of total cholesterol and the area under the concentration-time curve of apolipoprotein was calculated.

The lipid particle as reported herein, especially a lipid particle comprising a tetranectin-apolipoprotein of SEQ ID NO: 01 and POPC and DPPC at a molar ratio of 3:1, shows enhanced cholesterol mobilization in vivo.

Formation of Lipid Particles

For the formation of lipid particles as reported herein different methods are known, such as freeze-drying, freeze-thawing, detergent solubilization followed by dialysis, microfluidization, sonification, and homogenization.

For example aqueous mixtures of phospholipids with detergents can be incubated with purified apolipoprotein. The apolipoprotein can be added in native form. The detergent is afterwards removed by dialysis or diafiltration. The formation of lipid particles comprising the shortened tetranectin-apolipoprotein A-I fusion protein can be achieved by incubating the shortened tetranectin-apolipoprotein A-I fusion protein in monomeric or multimeric form with detergent solubilized lipids at their respective transition temperature. Removal of the detergent by dialysis results in the formation of lipid particles. A common method for the formation of lipid particles containing an apolipoprotein is based on the cholate method as described e.g. in Jonas, A., Methods Enzymol. 128 (1986) 553-582 or Experimental Lung Res. 6 (1984) 255-270. Removal of the detergent by dialysis results in the formation of lipid particles.

The main points which have to be considered for the lipid particle formation are i) the requirements for biological activity, and ii) technical requirements directed to the manufacturability of the lipid particle. For the formation of lipid particles comprising an apolipoprotein these requirements point in opposite directions.

From a technical point of view saturated phospholipids containing carboxylic acid moieties with a chain of 16 carbon atoms and shorter would be chosen (e.g. dipalmitoyl-sn-glycero-3-phosphocholine, DPPC; dimyristoyl-sn-glycero-3-phosphocholine, DMPC etc.). In contrast thereto from biological data it can be assumed that non-saturated phospholipids containing carboxylic acid moieties with a chain of at least 16 carbon atoms (e.g. palmitoyl-2-oleoyl-sn-glycero-3-phosphocholine, POPC; stearoyl-2-oleoyl-sn-glycero-3-phosphocholine, SOPC) are more effective and non-liver toxic.

The phosphatidylcholines DPPC and POPC and mixtures thereof can be used for the formation of lipid particles containing an apolipoprotein. These exemplary phosphatidylcholines differ in one carboxylic acid moiety and have one identical carboxylic acid moiety esterified to the phosphoglycerol backbone. The manufacture of lipid particles is easier when DPPC is used. In contrast POPC is more effective in in vitro functional assays, particularly as substrate for the activation of the lecithin cholesterol acetyl transferase (LCAT) enzyme which is necessary for the conversion of the mobilized cholesterol into cholesterol ester. It has been found that lipid particles comprising mixtures of two phosphatidylcholines, as e.g. POPC and DPPC, in different molar ratios have improved properties compared to lipid particles comprising only one phosphatidylcholine (see e.g. FIG. 4).

Different methods to reconstitute lipid particles from recombinant apolipoprotein or delipidated apolipoprotein derived from human HDL particles have been reported (HDL=high density lipoprotein). For example aqueous mixtures of phospholipids with detergents are incubated with purified apolipoprotein. The apolipoprotein is added in native form. The detergent is afterwards removed by dialysis or diafiltration. The formation of lipid particles comprising shortened tetranectin-apolipoprotein A-I fusion protein can be achieved by incubating the shortened tetranectin-apolipoprotein A-I fusion protein or a multimer thereof with detergent solubilized lipids at their respective transition temperature. Removal of the detergent by dialysis results in the formation of lipid particles.

The lipid particle can be purified by a combination of precipitation and/or chromatography steps. For example excess detergent, i.e. detergent not part of the lipid particle, can be removed in a hydrophobic adsorption chromatography step. The lipid particle can be recovered from the hydrophobic adsorption material with a detergent-free solution.

The following examples, sequence listing and figures are provided to aid the understanding of the present invention, the true scope of which is set forth in the appended claims. It is understood that modifications can be made in the procedures set forth without departing from the spirit of the invention.

DESCRIPTION OF THE SEQUENCE LISTING

SEQ ID NO: 01 Shortened tetranectin-apolipoprotein A-I fusion protein.
SEQ ID NO: 02 Human apolipoprotein A-I.
SEQ ID NO: 03 Human tetranectin trimerization domain.
SEQ ID NO: 04 Shortened human tetranectin trimerization domain.
SEQ ID NO: 05 Excised peptide.

EXEMPLIFICATION

Materials and Methods
Size-Exclusion-HPLC:

The chromatography was conducted with a Tosoh Haas TSK 3000 SWXL column on an ASI-100 HPLC system (Dionex, Idstein, Germany). The elution peaks were monitored at 280 nm by a UV diode array detector (Dionex). After dissolution of the concentrated samples to 1 mg/ml the column was washed with a buffer consisting of 200 mM potassium dihydrogen phosphate and 250 mM potassium chloride pH 7.0 until a stable baseline was achieved. The analyzing runs were performed under isocratic conditions using a flow rate of 0.5 ml/min. over 30 minutes at room temperature. The chromatograms were integrated manually with Chromeleon (Dionex, Idstein, Germany). Aggregation in % was determined by comparing the area under the curve (AUC) of high molecular weight forms with the AUC of the monomer peak.

Dynamic Light Scattering (DLS):

DLS is a non-invasive technique for measuring particle size, typically in the sub-micron size range. In the current invention the Zetasizer Nano S apparatus (Malvern Instruments, Worcestershire, UK) with a temperature controlled quartz cuvette (25° C.) was used for monitoring a size range between 1 nm and 6 μm. The intensity of the back scattered laser light was detected at an angle of 173°. The intensity fluctuates at a rate that is dependent upon the particle diffusion speed, which in turn is governed by particle size. Particle size data can therefore be generated from an analysis of the fluctuation in scattered light intensity (Dahneke, B. E. (ed.), Measurement of Suspended Particles by Quasielectric Light Scattering, Wiley Inc. (1983); Pecora, R., Dynamic Light Scattering: Application of Photon Correlation Spectroscopy, Plenum Press (1985)). The size distribution by intensity was calculated using the multiple narrow mode of the DTS software (Malvern). Experiments were conducted with undiluted samples.

SEC-MALLS:

SEC-MALLS is a combination of size exclusion chromatography with a three detector system: i) UV detection, ii) refraction index detection and iii) light scattering detection. For the separation by size a Superose 6 column 10/300 GL column from GE Healthcare is used. The method is run isocratically with a PBS buffer pH 7.4 applying a flow rate of 0.4 ml/min. Three detector systems are connected in series. The complete lipid particle (protein-lipid particle) signal is monitored by the refraction index detector whereas the UV absorbance determined at 280 nm determines the signal induced by the protein part. The proportion of the lipid fraction is obtained by a simple subtraction of the protein UV signal from the complete signal. Applying light scattering allows for the detection of the molecular mass of the respective species and, thus, a complete and detailed description of the lipid particle.

Detergent Determination:

The determination of residual detergent was conducted by reversed-phase chromatography coupled with an evaporative light scattering detector (RP-ELSD). As column a Luna C18 4.6×150 mm, 5 µm, 100 Å from Phenomenex (Aschaffenburg, Germany) was used. After centrifugation through a 10 kDa membrane 90 µl of the flow-through were used for HPLC separation. Elution was performed under isocratic conditions with 74% (v/v) methanol solution containing 0.1% (v/v) trifluoro acetic acid. Column temperature was set to 30° C. Detection was performed by an evaporative light scattering detector applying a nebulization temperature of 30° C., an evaporating temperature of 80° C. and a gas flow of 1.0 l/min. Quantification of the residual detergent was conducted by the establishment of a calibration curve, in case of cholate in the range of 0.22 µg to 7.5 µg cholate.

Protein Determination:

The protein concentration was determined by determining the optical density (OD) at 280 nm, using the molar extinction coefficient calculated on the basis of the amino acid sequence.

Recombinant DNA Technique:

Standard methods were used to manipulate DNA as described in Sambrook, J., et al., Molecular Cloning: A Laboratory Manual, 2nd edition, Cold Spring Harbor Laboratory Press, Cold Spring Harbor, N.Y. (1989). The molecular biological reagents were used according to the manufacturer's instructions.

Example 1

Making and Description of the *E. coli* Expression Plasmids

The shortened tetranectin-apolipoprotein A-I fusion protein was prepared by recombinant means. The expressed fusion protein has in N- to C-terminal direction the amino acid sequence of SEQ ID NO: 01.

The encoding fusion gene is assembled with known recombinant methods and techniques by connection of appropriate nucleic acid segments. Nucleic acid sequences made by chemical synthesis are verified by DNA sequencing. The expression plasmid for the production of the fusion protein of SEQ ID NO: 01 can be prepared as follows:

Plasmid 1 (1-pBRori-URA3-LACI-SAC) is an expression plasmid for the expression of core-streptavidin in *E. coli*. It was generated by ligation of the 3142 bp long EcoRI/CelII-vector fragment derived from plasmid 2 (2-pBRori-URA3-LACI-T-repeat; reported in EP-B 1 422 237) with a 435 bp long core-streptavidin encoding EcoRI/CelII-fragment.

The core-streptavidin *E. coli* expression plasmid comprises the following elements:
the origin of replication from the vector pBR322 for replication in *E. coli* (corresponding to bp position 2517-3160 according to Sutcliffe, G., et al., Quant. Biol. 43 (1979) 77-90),
the URA3 gene of *Saccharomyces cerevisiae* coding for orotidine 5'-phosphate decarboxylase (Rose, M., et al., Gene 29 (1984) 113-124) which allows plasmid selection by complementation of *E. coli* pyrF mutant strains (uracil auxotrophy),
the core-streptavidin expression cassette comprising
the T5 hybrid promoter (T5-PN25/03/04 hybrid promoter according to Bujard, H., et al., Methods. Enzymol. 155 (1987) 416-433 and Stueber, D., et al., Immunol. Methods IV (1990) 121-152) including a synthetic ribosomal binding site according to Stueber, D., et al. (see before),
the core-streptavidin gene,
two bacteriophage-derived transcription terminators, the λ-T0 terminator (Schwarz, E., et al., Nature 272 (1978) 410-414) and the fd-terminator (Beck, E. and Zink, B., Gene 1-3 (1981) 35-58),
the lacI repressor gene from *E. coli* (Farabaugh, P. J., Nature 274 (1978) 765-769).

The final expression plasmid for the expression of the shortened tetranectin-apolipoprotein A-I fusion protein can be prepared by excising the core-streptavidin structural gene from plasmid 1 using the singular flanking EcoRI and CelII restriction endonuclease cleavage site and inserting the EcoRII/CelII restriction site flanked nucleic acid encoding the fusion protein into the 3142 bp long EcoRI/CelII-1 plasmid fragment.

Example 2

Expression of Tetranectin-Apolipoprotein A-I

For the expression of the fusion proteins as reported herein an *E. coli* host/vector system which enables an antibiotic-free plasmid selection by complementation of an *E. coli* auxotrophy (PyrF) was employed (EP 0 972 838 and U.S. Pat. No. 6,291,245).

The *E. coli* K12 strain CSPZ-2 (leuB, proC, trpE, th-1, ΔpyrF) was transformed by electroporation with the expression plasmid. The transformed *E. coli* cells were first grown at 37° C. on agar plates.

For pre-fermentation a M9 medium according to Sambrook, et al. (Molecular Cloning: A Laboratory Manual, 2nd edition, Cold Spring Harbor Laboratory Press, Cold Spring Harbor, N.Y. (1989)) supplemented with about 1 g/l L-leucine, about 1 g/l L-proline and about 1 mg/l thiamine-HCl has been used.

For pre-fermentation 300 ml of M9-medium in a 1000 ml Erlenmeyer-flask with baffles was inoculated with 2 ml out of a primary seed bank ampoule. The cultivation was performed on a rotary shaker for 13 hours at 37° C. until an optical density (578 nm) of 1-3 was obtained.

For fermentation a batch medium according to Riesenberg, et al. was used (Riesenberg, D., et al., J. Biotechnol. 20 (1991) 17-27): 27.6 g/l glucose*$H_2O$, 13.3 g/l $KH_2PO_4$, 4.0 g/l $(NH_4)_2HPO_4$, 1.7 g/l citrate, 1.2 g/l $MgSO_4$*7 $H_2O$, 60 mg/l iron(III)citrate, 2.5 mg/l $CoCl_2$*6 $H_2O$, 15 mg/l $MnCl_2$*4 $H_2O$, 1.5 mg/l $CuCl_2$*2 $H_2O$, 3 mg/l $H_3BO_3$, 2.5 mg/l $Na_2MoO_4$*2 $H_2O$, 8 mg/l $Zn(CH_3COO)_2$*2 $H_2O$, 8.4 mg/l Titriplex III, 1.3 ml/l Synperonic 10% anti foam agent. The batch medium was supplemented with 5.4 mg/l Thiamin-HCl and 1.2 g/l L-leucine and L-proline respectively. The feed 1 solution contained 700 g/l glucose supplemented with 19.7 g/l $MgSO_4*7\ H_2O$. The alkaline solution for pH regulation was an aqueous 12.5% (w/v) $NH_3$ solution supplemented with 50 g/l L-leucine and 50 g/l L-proline respectively. All components were dissolved in deionized water.

The fermentation was carried out in a 10 l Biostat C DCU3 fermenter (Sartorius, Melsungen, Germany). Starting with 6.4 l sterile fermentation batch medium plus 300 ml inoculum from the pre-fermentation the batch fermentation was performed at 37° C., pH 6.9±0.2, 500 mbar and an aeration rate of 10 l/min. After the initially supplemented glucose was depleted the temperature was shifted to 28° C. and the fermentation entered the fed-batch mode. Here the relative value of dissolved oxygen (pO2) was kept at 50% (DO-stat, see e.g. Shay, L. K., et al., J. Indus. Microbiol. Biotechnol. 2 (1987) 79-85) by adding feed 1 in combination with constantly increasing stirrer speed (550 rpm to 1000 rpm within 10 hours and from 1000 rpm to 1400 rpm within 16 hours) and aeration rate (from 10 l/min to 16 l/min in 10 hours and from 16 l/min to 20 l/min in 5 hours). The supply with additional amino acids resulted from the addition of the alkaline solution, when the pH reached the lower regulation limit (6.70) after approximately 8 hours of cultivation. The expression of recombinant therapeutic protein was induced by the addition of 1 mM IPTG at an optical density of 70.

At the end of fermentation the cytoplasmatic and soluble expressed tetranectin-apolipoprotein A-I is transferred to insoluble protein aggregates, the so called inclusion bodies, with a heat step where the whole culture broth in the fermenter is heated to 50° C. for 1 or 2 hours before harvest (see e.g. EP-B 1 486 571). Thereafter, the content of the fermenter was centrifuged with a flow-through centrifuge (13,000 rpm, 13 l/h) and the harvested biomass was stored at -20° C. until further processing. The synthesized shortened tetranectin-apolipoprotein A-I fusion proteins were found exclusively in the insoluble cell debris fraction in the form of insoluble protein aggregates, so-called inclusion bodies (IBs).

Samples drawn from the fermenter, one prior to induction and the others at dedicated time points after induction of protein expression are analyzed with SDS-Polyacrylamide gel electrophoresis. From every sample the same amount of cells ($OD_{Target}$=5) are resuspended in 5 mL PBS buffer and disrupted via sonication on ice. Then 100 μL of each suspension are centrifuged (15,000 rpm, 5 minutes) and each supernatant is withdrawn and transferred to a separate vial. This is to discriminate between soluble and insoluble expressed target protein. To each supernatant (=soluble) fraction 300 μL and to each pellet (=insoluble) fraction 400 μL of SDS sample buffer (Laemmli, U.K., Nature 227 (1970) 680-685) are added. Samples are heated for 15 minutes at 95° C. under shaking to solubilize and reduce all proteins in the samples. After cooling to room temperature 5 μL of each sample are transferred to a 4-20% TGX Criterion Stain Free polyacrylamide gel (Bio-Rad). Additionally 5 μl molecular weight standard (Precision Plus Protein Standard, Bio-Rad) and 3 amounts (0.3 μl, 0.6 μl and 0.9 μl) quantification standard with known product protein concentration (0.1 μg/μl) are positioned on the gel.

The electrophoresis was run for 60 Minutes at 200 V and thereafter the gel was transferred the GelDOC EZ Imager (Bio-Rad) and processed for 5 minutes with UV radiation. Gel images were analyzed using Image Lab analysis software (Bio-Rad). With the three standards a linear regression curve was calculated with a coefficient of >0.99 and thereof the concentrations of target protein in the original sample was calculated.

Example 3

Preparation of Shortened Tetranectin-Apolipoprotein A-I Fusion Protein

Inclusion body preparation is carried out by resuspension of harvested bacteria cells in a Tris buffer solution (0.1 M, supplemented with 1 mM $MgSO_4$, pH 7.0). After the addition of DNAse the cell are disrupted by homogenization at a pressure of 900 bar. A buffer solution comprising 1.5 M NaCl and 60 mM EDTA is added to the homogenized cell suspension. After the adjustment of the pH value to 5.0 with 25% (w/v) HCl the final inclusion body slurry is obtained after a further centrifugation step. The slurry can be stored at -20° C. in single use, sterile plastic bags until further processing.

The inclusion body slurry (about 15 kg) is solubilized in an alkaline potassium hydrochloride solution and clarified by depth filtration. Alternatively the inclusion body slurry was solubilized in a guanidinium hydrochloride solution (150 l, 6.7 M).

Example 4

Refolding and Lipidation of the Shortened Tetranectin-Apolipoprotein A-I Fusion Protein a) General Cholate Method Pure crystalline POPC or DPPC (Lipoid, Switzerland) is dissolved in an aqueous buffer (lipidation buffer) containing cholate in a molar ratio phospholipid:cholate of 1:1.35. The mixtures are incubated under nitrogen atmosphere and protected from light at room temperature (POPC) or at 55° C. (DPPC) until a clear solution is obtained. The clear lipid-cholate solution is cooled to 4° C. (POPC) or stored at 41° C. (DPPC). Shortened tetranectin-apolipoprotein A-I fusion protein is added at 4° C. (POPC) or 41° C. (DPPC) at a defined apolipoprotein:phospholipid ratio. For lipid particle formation the reaction mixture is incubated over night at 4° C. (POPC) or 41° C. (DPPC) under nitrogen atmosphere and protected from light. Finally, cholate is removed by extensive dialysis (4° C./41° C.) against lipidation buffer. Finally samples are centrifuged to remove precipitated material.

Cholate solubilized lipid solutions containing POPC and DPPC can be prepared as described above. Lipid mixtures are prepared by combining the lipid solutions at the desired ratio followed by storage at the respective $T_m$ ($T_m$=phase transition temperature). Lipid particle formation of the shortened tetranectin-apolipoprotein A-I fusion protein is performed as described for pure lipid solutions but at the respective $T_m$ of the lipid mixture chosen.

The following lipidation buffers can be used:
1. 50 mM potassium phosphate buffer supplemented with 250 mM arginine hydrochloride, 7.5% sucrose at pH 7.5
2. 50 mM dipotassium hydrogen phosphate buffer supplemented with 250 mM arginine hydrochloride, 7.5% sucrose, 10 mM methionine at pH 7.5
3. 250 mM tris-hydroxylamino methane (TRIS) supplemented with 140 mM NaCl, 10 mM methionine at pH 7.5
4. 50 mM dipotassium hydrogen phosphate buffer supplemented with 250 mM arginine hydrochloride, 7% trehalose, 10 mM methionine at pH 7.5.

The homogeneity of the lipid particles formed comprising shortened tetranectin-apolipoprotein A-I fusion protein samples can be assessed by analytical SEC. Overall, the choice of the lipidation buffer has only a minor effect compared to the choice of phospholipid. DPPC-lipid particles elute as one main peak, whereas POPC-lipid particles shows a two peak pattern. Lipid particle formation was shown to be feasible irrespective of the lipidation buffer. Among various buffers tested the most appropriate lipidation buffer was identified to be 250 mM Tris, 140 mM NaCl, 10 mM methionine, pH 7.4.

Lipidation mixtures contained a defined amount of fusion protein and the amount of the respective phospholipid, e.g. POPC, is calculated accordingly. All calculations of the molar amount of lipid are based on the shortened tetranectin-apolipoprotein A-I fusion protein monomer.

Figure 11:
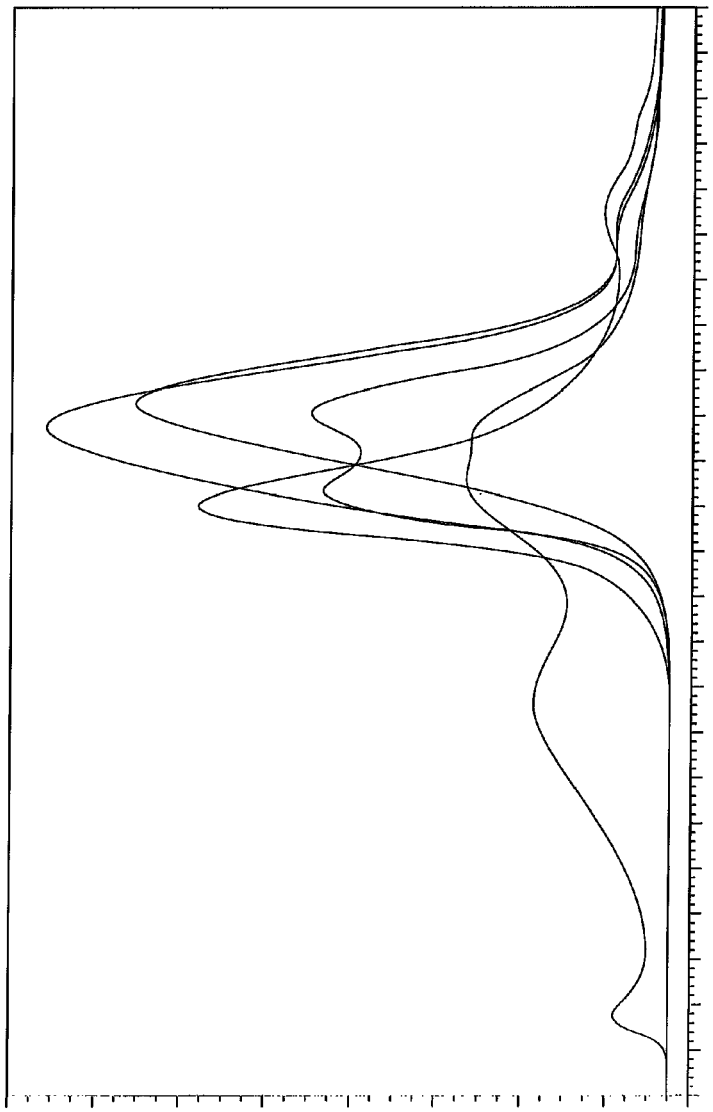
FIG. 11. SEC-MALLS analysis of lipid particles of POPC and tetranectin-apolipoprotein A-I in molar ratios of from 1:20 to 1:160.

SEC-MALLS analysis can be used to gain more detailed information on the homogeneity of the lipid particles and their apolipoprotein-phospholipid composition (protein-conjugate analysis). FIG. 11 shows an exemplary the chromatogram of SEC resolved samples (UV280 detection). Here the 1:160 sample is divided into three separated peaks. The 1:80 sample appeared to contain at least two species of different size as displayed as double peak. The peak obtained from sample 1:20 shows the most homogeneous product.

The protein-conjugate analysis enables the calculation of the total molecular weight of the protein (MW protein) and the lipid component (MW lipid) for each lipid particle eluted from the SEC column. Based on the molecular weights of the shortened tetranectin-apolipoprotein A-I fusion protein monomer (32.7 kDa) and POPC (760 Da) the composition of the lipid particle can be calculated (n protein and n POPC). The molecular weight of the apolipoprotein component found in the lipid particle main peak at all molar ratios is approximately 100 kDa corresponding to a shortened tetranectin-apolipoprotein A-I fusion protein trimer per lipid particle. The ratio n(POPC)/n(protein monomer) gives the number of POPC molecules per shortened tetranectin-apolipoprotein A-I fusion protein monomer in the lipid particle. The number of POPC molecules per shortened tetranectin-apolipoprotein A-I fusion protein monomer varies. The value % protein is a parameter for the degree of lipidation. The lower the percentage of the protein in the lipid particle, the higher the degree of lipidation.

B) Rapid Dilution Method for Refolding and Lipid Particle Formation with POPC and DPPC and Sodium Cholate Shortened tetranectin-apolipoprotein A-I fusion protein is expressed in *E. coli* and purified according to Examples 1 to 3. After purification, the buffer is exchanged by diafiltration into a solution containing 250 mM Tris, 140 mM NaCl, 6.7 M guanidinium hydrochloride, pH 7.4. The protein concentration was adjusted to about 30 mg/ml.

Two separate lipid stock solutions are prepared. Solution A is prepared by dissolving 100 moles/l of POPC in a buffer containing 250 mM Tris-HCl, 140 mM NaCl, 135 mM sodium cholate, pH 7.4 at room temperature. Solution B is prepared by dissolving 100 moles/l of DPPC in 250 mM Tris-HCl, 140 mM NaCl, 135 mM sodium cholate, pH 7.4 at 41° C. Lipid stock solutions A and B are mixed in a ratio of 3:1 and incubated for 2 hours at room temperature. Refolding buffer is prepared by diluting 384 ml of the lipid stock mixture into 6365 ml of 250 mM Tris-HCl, 140 mM NaCl, pH 7.4. This buffer is stirred for an additional 24 hours at room temperature.

Refolding and lipid particle formation is initiated by the addition of 750 ml shortened tetranectin-apolipoprotein A-I fusion protein comprising solution in 250 mM Tris, 140 mM NaCl, 6.7 M guanidinium hydrochloride, pH 7.4 to the refolding buffer. This results in a 1:10 dilution of the guanidinium hydrochloride. The solution is incubated at room temperature for at least 12 hours while constantly stirring. Detergent removal is carried out by diafiltration.

C) Lipid Particle Formation Starting from Denatured or Native Protein

The method as reported in item a) (first method) requires native apolipoprotein for lipid particle formation whereas the method reported in item b) (second method) starts with fully denatured apolipoprotein for lipid particle formation.

In an exemplary first method denatured shortened tetranectin-apolipoprotein A-I fusion protein in 6.7 M guanidinium hydrochloride, 50 mM Tris, 10 mM methionine, at pH 8.0 is extensively dialyzed against a buffer consisting of 250 mM Tris, 140 mM NaCl, 10 mM methionine, at pH 7.5 at a protein concentration of 3.46 mg/ml. A mixture of POPC and cholate is then added to yield a final concentration of 6 mM POPC and 8 mM cholate in the solution. This corresponds to a ratio of 60 molecules of POPC per molecule of shortened tetranectin-apolipoprotein A-I fusion protein monomer (60:1). The detergent is subsequently removed by diafiltration. Analysis of formed protein-lipid complexes is by SEC-MALLS. Using this method a heterogeneous product is formed.

In an exemplary second method denatured shortened tetranectin-apolipoprotein A-I fusion protein in 6.7 M guanidinium hydrochloride, 50 mM Tris, 10 mM methionine, at pH 8.0 is directly diluted 1:10 (v/v) into lipidation buffer resulting in a protein concentration of 2.5 mg/ml. The lipidation buffer is consisting of 6 mM cholate and 4.5 mM POPC corresponding to a lipid to protein ratio of 60:1. Using this method a homogenous product is formed.

d) 25% DPPC/75% POPC

The lipid particle formation was carried out accordingly as reported in item a) of this example with the following parameters:

| Protein: | shortened tetranectin-apolipoprotein A-I fusion protein |
|---|---|
| Lipidation buffer: | 250 mM Tris-HCl, 140 mM NaCl, 10 mM methionine, pH 7.4 |
| Lipidation: | at 18° C. |
| Dialysis: | at room temperature |
| Molar ratios tested: | 1:60 |

Lipid particle formation was straight forward. In the following Table the summary of SEC results are shown (percentages were calculated by integration of the AUC).

TABLE

| UV280 | Retention time Main peak [min] | Pre peak % | Main peak % | Post peak % | total [mAU * min] |
|---|---|---|---|---|---|
| 25/75 DPPC/POPC 1:60 | 58.2 | — | 90.2 | 9.8 | 342.6 |

Using a lipid mixture of 25% DPPC and 75% POPC for lipid particle formation of shortened tetranectin-apolipoprotein A-I fusion protein a homogeneous product was obtained at a molar ratio of 1:60 (protein to phospholipid). In the following Table the summary of protein conjugate analysis of lipid particles of 25% DPPC/75% POPC and shortened tetranectin-apolipoprotein A-I fusion protein at a molar ratio of 1:60 of protein to phospholipid is shown.

TABLE

| Example | | n (monomer)/ n(lipid) |
|---|---|---|
| 1 | Pre peak | 1:58 |
| | Main peak | 1:63 |
| | Post peak | 1:0 |

TABLE-continued

| Example | | n (monomer)/n(lipid) |
|---|---|---|
| 2 | Pre peak | 1:75 |
|   | Main peak | 1:67 |
|   | Post peak | 1:35 |
| 3 | Pre peak | 1:53 |
|   | Main peak | 1:59 |
|   | Post peak | 1:2 |
| 4 | Pre peak | 1:68 |
|   | Main peak | 1:65 |
|   | Post peak | 1:7 |
| 5 | Pre peak | 1:42 |
|   | Main peak | 1:59 |
|   | Post peak | 1:3 |
| 6 | Pre peak | 1:59 |
|   | Main peak | 1:52 |
|   | Post peak | 1:4 |

Example 5

Application of Apolipoprotein a) Impact of DPPC and POPC on LCAT Activity

Lipid particles comprising either palmitoyl oleoyl phosphatidylcholine (POPC) or dipalmitoyl phosphatidylcholine (DPPC) and either recombinant wild-type apolipoprotein A-I or a tetranectin-apolipoprotein A-I were can be examined for their ability to support cholesterol esterification by LCAT.

Tritiated cholesterol (4%; relative to the phosphatidylcholine content on a molar basis) is incorporated in the lipid particle by addition of an ethanolic cholesterol solution. The capacity of the resulting protein-lipid complex to support LCAT catalyzed cholesterol esterification is tested in presence of 0.2 μg/ml recombinant LCAT enzyme (ROAR biochemical) in 125 μl (10 mM Tris, 150 mM NaCl, 1 mM EDTA, 1 mM $NaN_3$; pH 7.4; 2 mg/ml HuFAF Albumin; 4 mM Beta mercapto-ethanol) for 1 hour at 37° C. The reaction is stopped by addition of chloroform:methanol (2:1) and lipids are extracted. "Percent" esterification is calculated after cholesterol—cholesteryl ester separation by TLC and scintillation counting. If 20% or less of the tracer is incorporated into the formed ester, the reaction rate can be considered constant under the experimental conditions. Exemplary data are fitted to the Michaelis Menten equation using XLfit software (IDBS). For a visualization of the results obtained with a tetranectin-apolipoprotein A-I fusion protein with an amino acid sequence of SEQ ID NO: 01 and an additional N-terminal alanine amino acid residue see FIG. 3.

b) Impact of DPPC/POPC Mixtures on LCAT Activity

Lipid particles are prepared using cholate as detergent by mixing recombinant wild-type apolipoprotein A-I with $^3$H-cholesterol, a DPPC/POPC mixture, and cholate in 1:4:80:113 molar ratios. DPPC/POPC mixtures contained either 100% POPC; 75% POPC; 50% POPC; 25% POPC.

Figure 4:
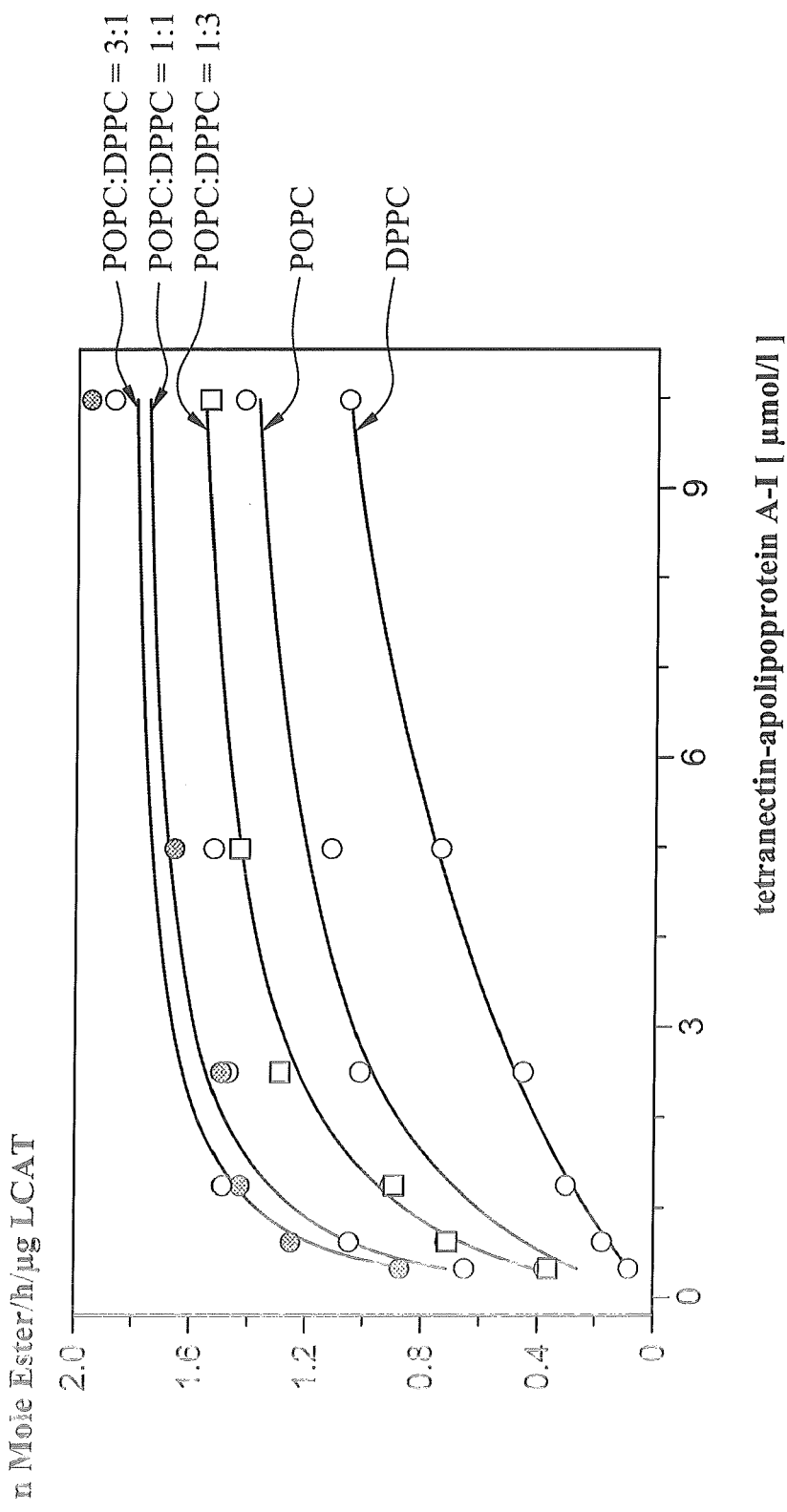
FIG. 4. Initial velocity of cholesterol esterification in lipid particles containing POPC and/or DPPC.

After cholate removal by dialysis, the capacity of the resulting protein-lipid complex to support LCAT catalyzed cholesterol esterification is tested. $^3$H-cholesterol (4%; relative to the phosphatidylcholine content on a molar basis) is incorporated in the lipid particle by addition of an ethanolic cholesterol solution. The capacity of the resulting protein-lipid complex to support LCAT catalyzed cholesterol esterification is tested in presence of 0.2 μg/ml recombinant LCAT enzyme (ROAR biochemical) in 125 μl (10 mM Tris, 150 mM NaCl, 1 mM EDTA, 1 mM $NaN_3$; pH 7.4; 2 mg/ml HuFAF Albumin; 4 mM beta mercaptoethanol) for 1 hour at 37° C. The reaction is stopped by addition of chloroform:methanol (2:1) and lipids are extracted. "Percent" esterification is calculated after cholesterol—cholesteryl ester separation by TLC and scintillation counting. If less than 20% of the tracer is incorporated into esters, the reaction rate can be considered as constant in the experimental conditions. Exemplary data are fitted to the Michaelis Menten equation using XLfit software (IDBS) and are shown in FIG. 4 for a tetranectin-apolipoprotein A-I fusion protein with an amino acid sequence of SEQ ID NO: 01 and an additional N-terminal alanine amino acid residue.

c) Cholesterol Efflux to THP-1 Derived Foam Cells

Macrophage like human THP-1 cells, can be obtained by exposing THP-1 monocytic leukemia cells to phorbol myristate acetate. Subsequently cells are loaded by further culture in the presence of acetylated LDL containing $^3$H-cholesterol tracer. These model foam cells are afterwards exposed for 4 h-8 h to cholesterol acceptor test compounds (see below). Cell culture supernatants are harvested and cells lysed in 5% NP40. Fractional efflux is calculated as the ratio of cholesterol radioactivity in the supernatant relative to the sum of the radioactivity in the cells plus supernatant. Efflux from cell exposed to medium containing no acceptors is subtracted and efflux velocity calculated by linear fit. Efflux velocity is standardized using efflux from cells to 10 μg/ml wild-type apolipoprotein A-I as reference (relative efflux velocity). Relative efflux velocities obtained in two separate experiments can be plotted as function of cholesterol acceptor concentration and data fitted to the Michaelis Menten equation. Parallel experiments can be performed using cells exposed to a RXR-LXR agonist that is known to upregulate ABCA-1 transporters, and bias cholesterol transport toward ABCA-1 mediated efflux.

Only a modest influence of the lipid mixture was observed in the tested series with a tetranectin-apolipoprotein A-I fusion protein with an amino acid sequence of SEQ ID NO: 01 and an additional N-terminal alanine amino acid residue (exemplary data shown in FIG. 5).

d) In Vivo Study

Five lipid particle variants comprising a tetranectin-apolipoprotein A-I fusion protein with an amino acid sequence of SEQ ID NO: 01 and an additional N-terminal alanine amino acid residue are studied:

i) only POPC ii) only DPPC iii) POPC:DPPC 3:1 iv) POPC:DPPC 1:1 v) DPPC:SM 9:1

Rabbits are intravenous infused over 0.5 h at 80 mg/kg (n=3 rabbits/test compound) followed by serial blood sampling over 96 h post infusion.

Analysis of apolipoprotein levels with an ELISA:

drug levels data on plasma values of liver enzymes, cholesterol, cholesterol ester.

Plasma concentrations are very similar for all tested compositions showing little pronounced initial "distribution" phase followed by log-linear decline of concentrations (FIG. 7). The following Table shows the pharmacokinetic data for a tetranectin-apolipoprotein A-I fusion protein with an amino acid sequence of SEQ ID NO: 01 and an additional N-terminal alanine amino acid residue.

TABLE

| tetranectin-apolipoprotein A-I with | $C_L$ [ml/h/kg] | $V_{ss}$ [ml/kg] | $T_{1/2}$ [h] | $C_{max}$ [mg/m] |
|---|---|---|---|---|
| 100% POPC/ 0% DPPC | 0.897 ± 0.216 | 45.0 ± 2.5 | 36.9 ± 8.2 | 2.40 ± 0.19 |
| 0% POPC/ 100% DPPC | 0.922 ± 0.098 | 37.8 ± 4.9 | 30.2 ± 7.7 | 2.29 ± 0.19 |
| 75% POPC/ 25% DPPC | 0.815 ± 0.064 | 37.8 ± 5.6 | 34.2 ± 4.5 | 2.65 ± 0.28 |
| 50% POPC/ 50% DPPC | 0.850 ± 0.135 | 43.1 ± 5.9 | 38.6 ± 10.6 | 2.34 ± 0.31 |
| 90% DPPC/ 10% SM | 1.28 ± 0.62 | 50.7 ± 8.7 | 31.3 ± 8.2 | 1.91 ± 0.33 |

The determined pharmacokinetic (PK) parameters are similar for all tested compounds. Also a low inter-individual variability has been found. The determined half-lives are close to 1.5 days, i.e. increased compared to wild-type apolipoprotein A-I. The volume of distribution is similar to plasma volume (ca. 40 ml/kg in rabbits).

f) Cholesterol Mobilization

Cholesterol is mobilized and esterified in plasma. Plasma cholesteryl ester levels do continue to increase even after tetranectin-apolipoprotein A-I is already decreasing. When plasma tetranectin-apolipoprotein A-I levels have decreased to 0.5 mg/ml (about 50% of normal wild-type apolipoprotein A-I) increased cholesterol ester levels are still detectable for a tetranectin-apolipoprotein A-I fusion protein with an amino acid sequence of SEQ ID NO: 01 and an additional N-terminal alanine amino acid residue (FIG. 8).

g) Liver Enzyme Release

Lipid particles comprising a tetranectin-apolipoprotein A-I fusion protein with an amino acid sequence of SEQ ID NO: 01 and an additional N-terminal alanine amino acid residue containing POPC do not induce liver enzyme release (see FIG. 1). Similar to the rabbit, a single i.v. injection of the tetranectin-apolipoprotein A-I containing POPC or POPC/DPPC mixtures are safe in mice. The apolipoprotein composition containing DPPC:POPC at a molar ratio of 1:3 is comparable to POPC alone (FIG. 9).

No significant hemolysis is observed until two hours post infusion in any of the five preparations. Hemolysis is determined photometrically as red color in plasma samples obtained at two hours after i.v. application of tetranectin-apolipoprotein A-I. 100% hemolysis of whole blood (generated by 0.44% Triton X-100-final concentration) is used for calibration (FIG. 10).

H) Anti-Inflammatory Effects of Tetranectin-Apolipoprotein A-I on Human Umbilical Vein Endothelial Cells Passage 5-10 HUVECs (human umbilical vein endothelial cells) are incubated in the respective tetranectin-apolipoprotein A-I fusion protein (tetranectin-apolipoprotein A-I fusion protein with an amino acid sequence of SEQ ID NO: 01 and an additional N-terminal alanine amino acid residue) preparations for 16 hours and stimulated with TNFα for the final 4 hours. VCAM1 surface expression is detected with specific antibodies by FACS.

Example 6

Lipid Particle Stability

Wild-type apolipoprotein A-I containing an N-terminal histidine-tag and an IgA protease cleavage site can be expressed in *E. coli* and purified by column chromatography as reported in the examples above. The histidine-tag is removed by IgA protease cleavage, which results in a tetranectin-apolipoprotein A-I fusion protein with an amino acid sequence of SEQ ID NO: 02 and an additional N-terminal alanine amino acid residue. Lipid particles (HDL particles) are assembled using a 1:150 ratio of protein to Lipoid S100 soybean phospholipid mixture. The particles are stored in a buffer containing 5 mM sodium phosphate and 1% sucrose at pH value of 7.3. SE-HPLC revealed three distinct peaks upon incubation after lipidation and incubation for 10 days. After incubation at 40° C., a predominant peak at retention time 10.8 minutes can be detected (47% of total protein), which is absent in the sample stored at 5° C. The 10.8 minutes peak indicates the formation of soluble large molecular weight assemblies due to protein destabilization.

HDL particles containing tetranectin-apolipoprotein A-I fusion protein with an amino acid sequence of SEQ ID NO: 01 and an additional N-terminal alanine residue, which are obtained starting from a POPC:DPPC mixture (ratio POPC to DPPC of 3:1), are also incubated at 5° C. and 40° C. Incubation at elevated temperature leads to a slight degree of pre-peak formation, but no significant shift to high molecular weight assemblies at 10.8 minutes (<2% increase at 11 minutes). This should indicate improved HDL particle stability compared to the particle containing wild-type apolipoprotein A-I.

Example 7

Cholesterol Mobilization

The efficiency at which cholesterol is mobilized into the blood can be determined by comparing the respective excursion of total cholesterol with apolipoprotein concentrations after administration of apolipoprotein in vivo. For a quantitative assessment, the quotient of the baseline corrected area under the concentration-time curve (AUC) of total cholesterol and the area under the concentration-time curve of apolipoprotein was calculated.

In this experiment the following substances were analyzed:
wild-type apolipoprotein A-I containing an N-terminal histidine-tag and an IgA protease cleavage site expressed in *E. coli* and purified by column chromatography as reported in the examples above; the histidine-tag was removed by IgA protease cleavage; lipid particles (HDL particles) were assembled using a 1:150 ratio of protein to Lipoid S100 soybean phospholipid mixture,
apolipoprotein A-I Milano variant; lipid particles (HDL particles) were assembled using a 1:40 ratio of protein to POPC,
tetranectin-apolipoprotein A-I of SEQ ID NO: 02; lipid particles (HDL particles) were assembled using a 1:60 ratio of protein to POPC and DPPC (POPC and DPPC at a ratio of 3:1).

The three HDL particles were applied to rats. The values obtained for the respective AUC ratios are shown in the following Table.

TABLE

| | lipids | AUC (time dependent concentration cholesterol in blood) AUC (time dependent apolipoprotein A-I concentration in blood) |
|---|---|---|
| wt-apolipoprotein A-I | soybean phospholipid mixture | 0.0002 (mmol/l)/(μg/ml)) |
| apolipoprotein A-I Milano variant | POPC | 0.0004 (mmol/l)/(μg/ml)) |
| tetranectin-apolipoprotein A-I as reported herein | POPC:DPPC 3:1 | 0.0013 (mmol/l)/(μg/ml) |

What is claimed is:

1. A fusion protein comprising the amino acid sequence of SEQ ID NO: 01 or a variant thereof having at least 70% sequence identity with the amino acid sequence of SEQ ID NO: 01, wherein the first four amino acid residues of the fusion protein are PIVN (residues 1-4 of SEQ ID NO: 01).

2. A lipid particle comprising a fusion protein of claim 1.

3. The lipid particle of claim 2, further comprising
   a phosphatidylcholine, and
   a lipid.

4. The lipid particle of claim 2, further comprising
   a first phosphatidylcholine, and
   a second phosphatidylcholine.

5. The lipid particle of claim 4, comprising 1-palmitoyl-2-oleoyl-phosphatidylcholine and 1,2-dipalmitoyl-phosphatidylcholine.

6. The lipid particle of claim 5, wherein the molar ratio of 1-palmitoyl-2-oleoyl-phosphatidylcholine to 1,2-dipalmitoyl-phosphatidylcholine is from 99:1 to 25:75.

7. The lipid particle of claim 2, wherein the fusion protein is a multimer comprising three monomers.

8. The lipid particle of claim 2, wherein the lipid particle binds to a receptor selected from the group consisting of cubilin, Scavenger receptor class B, type 1 (SR-BI), ATP-binding cassette 1 (ABCA-1), Lecithin-cholesterol acyltransferase (LCAT), Cholesteryl-ester transfer protein (CETP), or Phospholipid transfer protein (PLTP).

9. The lipid particle of claim 4, wherein the number of phospholipid molecules per apolipoprotein monomer in the lipid particle is from 40 to 120.

10. The lipid particle of claim 9, wherein the number of phospholipid molecules per apolipoprotein monomer in the lipid particle is from 50 to 90.

11. A pharmaceutical composition comprising (i) a fusion protein of claim 1, or (ii) a lipid particle comprising a fusion protein of claim 1.

12. A method for
    treatment of atherosclerosis,
    inducing reverse cholesterol transport and/or plaques pacification,
    cleaning/dissolution/stabilization of atherosclerotic plaques in blood vessels of a subject or for redistributing cholesterol from the wall of arteries to the liver of a subject,
    treating a valvular stenosis in a subject,
    increasing the number of HDL particles in a subject,
    initiation of reverse cholesterol transport in a subject,
    the removal of endotoxins,
    the treatment of angina pectoris,
    the treatment of myocardial infarction,
    the treatment of unstable angina pectoris,
    the treatment of arterial stenoses such as peripheral artery diseases (PAD), carotis stenosis, cerebral arterial stenosis or coronary arterial stenosis,
    the treatment of vascular demencia, or
    the treatment of amaurosis fugax,
    wherein the method comprises administering to a patient in need thereof an effective amount of (i) a fusion protein of claim 1, or (ii) a lipid particle comprising a fusion protein of claim 1.

13. The method of claim 12, wherein the fusion protein or lipid particle is administered in an amount sufficient to induce reverse cholesterol transport and/or plaques pacification in a subject.

14. A method for treating:
acute coronary syndrome,
atherosclerosis,
atherosclerotic plaques in blood vessels of a subject,
valvular stenosis in a subject,
septic shock,
angina pectoris,
myocardial infarction,
unstable angina pectoris,
arterial stenoses,
peripheral artery diseases (PAD),
carotis stenosis,
cerebral arterial stenosis,
coronary arterial stenosis,
vascular demencia, or
amaurosis fugax,
wherein the method comprises administering to a patient in need thereof an effective amount of (i) a fusion protein of claim 1, or (ii) a lipid particle comprising a fusion protein of claim 1.

15. A method for:
inducing reverse cholesterol transport,
inducing plaques pacification,
cleaning or dissoluting or stabilizing atherosclerotic plaques,
redistributing cholesterol from the wall of arteries to the liver,
increasing the number of HDL particles,
removal of endotoxins,
wherein the method comprises administering to a patient in need thereof an effective amount of (i) a fusion protein of claim 1, or (ii) a lipid particle comprising a fusion protein of claim 1.

16. A method of inducing reverse cholesterol transport, or inducing plaques pacification, or cleaning or dissoluting or stabilizing atherosclerotic plaques, or redistributing cholesterol from the wall of arteries to the liver, or increasing the number of HDL particles, or removing endotoxins in an individual, comprising administering to the individual an effective amount of a fusion protein of claim 1 or a lipid particle comprising a fusion protein of claim 1 to induce reverse cholesterol transport, or to induce plaques pacification, or to clean or dissolute or stabilize atherosclerotic plaques, or to redistribute cholesterol from the wall of arteries to the liver, or to increase the number of HDL particles, or to remove endotoxins.

* * * * *

SEQUENCE LISTING

<160> NUMBER OF SEQ ID NOS: 7

<210> SEQ ID NO 1
<211> LENGTH: 284
<212> TYPE: PRT
<213> ORGANISM: Artificial Sequence
<220> FEATURE:
<223> OTHER INFORMATION: Tetranectin-apolipoprotein A-I (1)

<400> SEQUENCE: 1

```
Pro Ile Val Asn Ala Lys Lys Asp Val Val Asn Thr Lys Met Phe Glu
1               5                   10                  15

Glu Leu Lys Ser Arg Leu Asp Thr Leu Ala Gln Glu Val Ala Leu Leu
            20                  25                  30

Lys Glu Gln Gln Ala Leu Gln Thr Val Asp Glu Pro Pro Gln Ser Pro
        35                  40                  45

Trp Asp Arg Val Lys Asp Leu Ala Thr Val Tyr Val Asp Val Leu Lys
    50                  55                  60

Asp Ser Gly Arg Asp Tyr Val Ser Gln Phe Glu Gly Ser Ala Leu Gly
65                  70                  75                  80

Lys Gln Leu Asn Leu Lys Leu Leu Asp Asn Trp Asp Ser Val Thr Ser
                85                  90                  95

Thr Phe Ser Lys Leu Arg Glu Gln Leu Gly Pro Val Thr Gln Glu Phe
            100                 105                 110

Trp Asp Asn Leu Glu Lys Glu Thr Glu Gly Leu Arg Gln Glu Met Ser
        115                 120                 125

Lys Asp Leu Glu Glu Val Lys Ala Lys Val Gln Pro Tyr Leu Asp Asp
    130                 135                 140

Phe Gln Lys Lys Trp Gln Glu Glu Met Glu Leu Tyr Arg Gln Lys Val
145                 150                 155                 160

Glu Pro Leu Arg Ala Glu Leu Gln Glu Gly Ala Arg Gln Lys Leu His
                165                 170                 175

Glu Leu Gln Glu Lys Leu Ser Pro Leu Gly Glu Glu Met Arg Asp Arg
            180                 185                 190

Ala Arg Ala His Val Asp Ala Leu Arg Thr His Leu Ala Pro Tyr Ser
        195                 200                 205

Asp Glu Leu Arg Gln Arg Leu Ala Ala Arg Leu Glu Ala Leu Lys Glu
    210                 215                 220

Asn Gly Gly Ala Arg Leu Ala Glu Tyr His Ala Lys Ala Thr Glu His
225                 230                 235                 240

Leu Ser Thr Leu Ser Glu Lys Ala Lys Pro Ala Leu Glu Asp Leu Arg
                245                 250                 255

Gln Gly Leu Leu Pro Val Leu Glu Ser Phe Lys Val Ser Phe Leu Ser
            260                 265                 270

Ala Leu Glu Glu Tyr Thr Lys Lys Leu Asn Thr Gln
        275                 280
```

<210> SEQ ID NO 2
<211> LENGTH: 267
<212> TYPE: PRT
<213> ORGANISM: Homo sapiens

<400> SEQUENCE: 2

```
Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30
```

-continued

```
Asp Arg Val Lys Asp Leu Ala Thr Val Tyr Val Asp Val Leu Lys Asp
        35                  40                  45

Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Glu Met Glu Leu Tyr Arg Gln Lys Val Glu
    130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
    210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln
                260                 265

<210> SEQ ID NO 3
<211> LENGTH: 51
<212> TYPE: PRT
<213> ORGANISM: Homo sapiens
<300> PUBLICATION INFORMATION:
<302> TITLE: Trimerising module
<310> PATENT DOCUMENT NUMBER: WO 98/56906
<311> PATENT FILING DATE: 1998-06-11
<312> PUBLICATION DATE: 1998-12-17
<313> RELEVANT RESIDUES IN SEQ ID NO: (1)..(51)

<400> SEQUENCE: 3

Glu Pro Pro Thr Gln Lys Pro Lys Lys Ile Val Asn Ala Lys Lys Asp
1               5                   10                  15

Val Val Asn Thr Lys Met Phe Glu Glu Leu Lys Ser Arg Leu Asp Thr
            20                  25                  30

Leu Ala Gln Glu Val Ala Leu Leu Lys Glu Gln Gln Ala Leu Gln Thr
        35                  40                  45

Val Cys Leu
    50

<210> SEQ ID NO 4
<211> LENGTH: 40
<212> TYPE: PRT
<213> ORGANISM: Homo sapiens

<400> SEQUENCE: 4
```

```
Ile Val Asn Ala Lys Lys Asp Val Val Asn Thr Lys Met Phe Glu Glu
1               5                   10                  15

Leu Lys Ser Arg Leu Asp Thr Leu Ala Gln Glu Val Ala Leu Leu Lys
            20                  25                  30

Glu Gln Gln Ala Leu Gln Thr Val
            35                  40

<210> SEQ ID NO 5
<211> LENGTH: 5
<212> TYPE: PRT
<213> ORGANISM: Homo sapiens

<400> SEQUENCE: 5

Ser Leu Lys Gly Ser
1               5

<210> SEQ ID NO 6
<211> LENGTH: 5
<212> TYPE: PRT
<213> ORGANISM: Homo sapiens

<400> SEQUENCE: 6

Ala Pro Ile Val Asn
1               5

<210> SEQ ID NO 7
<211> LENGTH: 6
<212> TYPE: PRT
<213> ORGANISM: Homo sapiens

<400> SEQUENCE: 7

Met Ala Pro Ile Val Asn
1               5
```